(12) United States Patent
O'Donnell et al.

(10) Patent No.: US 9,041,150 B2
(45) Date of Patent: May 26, 2015

(54) VERTICALLY INTEGRATED SYSTEMS

(71) Applicant: Analog Devices, Inc., Norwood, MA (US)

(72) Inventors: Alan J. O'Donnell, Castletroy (IE); Santiago Iriarte, Dooradoyle (IE); Mark J. Murphy, Kilmore (IE); Colin G. Lyden, Baltimore (IE); Gary Casey, Prospect (IE); Eoin Edward English, Pallasgreen (IE)

(73) Assignee: Analog Devices, Inc., Norwood, MA (US)

( * ) Notice: Subject to any disclaimer, the term of this patent is extended or adjusted under 35 U.S.C. 154(b) by 0 days.

(21) Appl. No.: 14/041,780

(22) Filed: Sep. 30, 2013

(65) Prior Publication Data
US 2014/0026649 A1    Jan. 30, 2014

Related U.S. Application Data

(63) Continuation of application No. 12/975,847, filed on Dec. 22, 2010, now Pat. No. 8,569,861.

(51) Int. Cl.
*H01L 25/16* (2006.01)
*H01L 23/488* (2006.01)
(Continued)

(52) U.S. Cl.
CPC ............ *G01N 27/4148* (2013.01); *H01L 25/16* (2013.01); *H01L 2924/09701* (2013.01); *H01L 2224/0557* (2013.01); *H01L 2924/19104* (2013.01); *H01L 23/3677* (2013.01); *H01L 23/38* (2013.01); *H01L 23/473* (2013.01); *H01L 23/481* (2013.01); *H01L 2924/10253* (2013.01); *B81B 7/00* (2013.01); *G01N 27/26* (2013.01); *H01L 25/167* (2013.01); *H01L 27/14* (2013.01);
(Continued)

(58) Field of Classification Search
USPC ............ 257/529, 532, 531, 536, 82, E29.326, 257/E29.342, E23.149, E33.077, E29.325
See application file for complete search history.

(56) References Cited

U.S. PATENT DOCUMENTS

| 6,075,239 A | 6/2000 | Aksyuk et al. |
|---|---|---|
| 6,765,287 B1 | 7/2004 | Lin |

(Continued)

FOREIGN PATENT DOCUMENTS

| CN | 1877989 | 12/2006 |
|---|---|---|
| EP | 1 732 215 | 12/2006 |

(Continued)

OTHER PUBLICATIONS

F. Roozeboom et al., "System-in-Package Integration of Passives using 3D Through-Silicon Vias", Solid State Technology, May 2008, vol. 51, No. 5, pp. 38-47.

(Continued)

*Primary Examiner* — Mamadou Diallo
(74) *Attorney, Agent, or Firm* — Knobbe, Martens, Olson & Bear, LLP

(57) ABSTRACT

Embodiments of the present invention provide an integrated circuit system including a first active layer fabricated on a front side of a semiconductor die and a second pre-fabricated layer on a back side of the semiconductor die and having electrical components embodied therein, wherein the electrical components include at least one discrete passive component. The integrated circuit system also includes at least one electrical path coupling the first active layer and the second pre-fabricated layer.

38 Claims, 41 Drawing Sheets

(51) Int. Cl.

| | | |
|---|---|---|
| *G01N 27/414* | (2006.01) | |
| *H01L 23/48* | (2006.01) | |
| *B81B 7/00* | (2006.01) | |
| *G01N 27/26* | (2006.01) | |
| *H01L 27/14* | (2006.01) | |
| *H01L 27/15* | (2006.01) | |
| *H01L 49/02* | (2006.01) | |
| *H01L 31/0392* | (2006.01) | |
| *H01F 17/00* | (2006.01) | |
| *H01L 21/82* | (2006.01) | |
| *H01L 27/06* | (2006.01) | |
| *H01L 23/00* | (2006.01) | |
| *H01F 17/04* | (2006.01) | |
| *H02S 40/38* | (2014.01) | |
| *H02S 10/10* | (2014.01) | |
| *H01L 31/053* | (2014.01) | |
| *H01L 23/367* | (2006.01) | |
| *H01L 23/38* | (2006.01) | |
| *H01L 23/473* | (2006.01) | |

(52) U.S. Cl.
CPC ............... *H01L 27/15* (2013.01); *H01L 28/00* (2013.01); *H01L 31/0392* (2013.01); *H01F 17/00* (2013.01); *H01L 28/10* (2013.01); *H01L 28/20* (2013.01); *H01L 28/60* (2013.01); *H01L 28/82* (2013.01); *H01L 28/86* (2013.01); *H01L 28/90* (2013.01); *H01L 21/82* (2013.01); *H01L 27/0694* (2013.01); *Y02E 10/50* (2013.01); *H01L 24/48* (2013.01); *H01L 2224/48265* (2013.01); *H01F 17/04* (2013.01); *H02S 40/38* (2014.12); *H02S 10/10* (2014.12); *H01L 2224/0556* (2013.01); *H01L 24/05* (2013.01); *H01L 24/13* (2013.01); *H01L 24/94* (2013.01); *H01L 2224/48091* (2013.01); *H01L 2924/00014* (2013.01); *H01L 2924/1461* (2013.01); *H01L 2224/05554* (2013.01); *H01L 31/0583* (2013.01); *H01L 31/0586* (2013.01)

(56) References Cited

U.S. PATENT DOCUMENTS

| | | | |
|---|---|---|---|
| 6,800,930 B2 | 10/2004 | Jackson et al. | |
| 6,803,559 B2 | 10/2004 | Hsu et al. | |
| 6,879,429 B2 | 4/2005 | Wong et al. | |
| 7,130,177 B2 | 10/2006 | Aizawa et al. | |
| 7,208,832 B2 | 4/2007 | Yamagata | |
| 7,550,834 B2 | 6/2009 | Yu et al. | |
| 7,648,911 B2 | 1/2010 | Pagaila et al. | |
| 7,691,747 B2 | 4/2010 | Lin et al. | |
| 7,723,831 B2 | 5/2010 | Kwang et al. | |
| 7,855,429 B2 | 12/2010 | Ishida et al. | |
| 8,101,898 B2 | 1/2012 | Koste et al. | |
| 8,274,147 B2 | 9/2012 | Rofougaran et al. | |
| 8,280,207 B2 | 10/2012 | Pinguet et al. | |
| 8,339,798 B2 | 12/2012 | Minoo et al. | |
| 8,350,382 B2 | 1/2013 | Furgut et al. | |
| 8,362,589 B2 | 1/2013 | Quinn | |
| 8,368,654 B2 | 2/2013 | Rosenblatt et al. | |
| 8,390,083 B2 | 3/2013 | O'Donnell et al. | |
| 8,395,252 B1 | 3/2013 | Yang | |
| 8,402,666 B1 | 3/2013 | Hsu et al. | |
| 8,436,690 B2 | 5/2013 | McCraith et al. | |
| 8,436,698 B2 | 5/2013 | Rogers | |
| 8,569,861 B2 | 10/2013 | O'Donnell et al. | |
| 8,637,943 B1 | 1/2014 | Yang | |
| 2005/0253244 A1 | 11/2005 | Chang | |
| 2006/0139883 A1* | 6/2006 | Hu et al. | 361/699 |
| 2006/0258053 A1 | 11/2006 | Lee et al. | |
| 2006/0261460 A1 | 11/2006 | Sato et al. | |
| 2007/0187826 A1 | 8/2007 | Shim et al. | |
| 2007/0210423 A1 | 9/2007 | Hsu | |
| 2007/0246806 A1 | 10/2007 | Ong et al. | |
| 2007/0246813 A1 | 10/2007 | Ong et al. | |
| 2007/0296065 A1 | 12/2007 | Yew et al. | |
| 2008/0054431 A1 | 3/2008 | Wang et al. | |
| 2008/0265421 A1 | 10/2008 | Brunnbauer et al. | |
| 2009/0008792 A1 | 1/2009 | Ko et al. | |
| 2009/0029492 A1 | 1/2009 | Tu et al. | |
| 2009/0039492 A1 | 2/2009 | Kang et al. | |
| 2009/0079065 A1 | 3/2009 | Furgut et al. | |
| 2009/0170242 A1 | 7/2009 | Lin et al. | |
| 2009/0194829 A1 | 8/2009 | Chung et al. | |
| 2009/0261460 A1 | 10/2009 | Kuan et al. | |
| 2009/0283871 A1 | 11/2009 | Chang et al. | |
| 2009/0302437 A1 | 12/2009 | Kim et al. | |
| 2009/0321930 A1 | 12/2009 | Marcoux | |
| 2010/0032748 A1 | 2/2010 | Edwards | |
| 2010/0044704 A1 | 2/2010 | Male et al. | |
| 2010/0171203 A1 | 7/2010 | Chen et al. | |
| 2010/0193905 A1 | 8/2010 | Kim et al. | |
| 2011/0023929 A1 | 2/2011 | Edwards | |
| 2011/0057273 A1 | 3/2011 | O'Donnell et al. | |
| 2011/0199057 A1 | 8/2011 | Ivanov et al. | |
| 2013/0250532 A1 | 9/2013 | Bryzek et al. | |
| 2013/0273693 A1 | 10/2013 | Haba et al. | |
| 2013/0299924 A1 | 11/2013 | Weber et al. | |
| 2014/0014480 A1 | 1/2014 | Anderson et al. | |
| 2014/0034104 A1 | 2/2014 | O'Donnell et al. | |
| 2014/0035630 A1 | 2/2014 | O'Donnell et al. | |
| 2014/0103540 A1 | 4/2014 | Ching et al. | |

FOREIGN PATENT DOCUMENTS

| | | |
|---|---|---|
| JP | 2004-349537 | 12/2004 |
| JP | 2005-353867 | 12/2005 |
| JP | 2006-245311 | 9/2006 |
| JP | 2006-344737 | 12/2006 |
| JP | 2007-103413 | 4/2007 |
| JP | 2008-017421 | 1/2008 |
| JP | 2009-200189 | 9/2009 |
| JP | 2010-087021 | 4/2010 |
| JP | 2010-251662 | 11/2010 |
| KR | 2006-0045375 | 5/2006 |
| KR | 2009-0117004 | 11/2009 |
| WO | 2005/101476 | 10/2005 |

OTHER PUBLICATIONS

M. Duplessis et al., "Physical Implementation of 3D Integrated Solenoids within Silicon Substrate for Hybrid IC Applications", IEEE European Microwave Conference, Oct. 2009, pp. 1006-1009.

H.B. Fan et al., "Prediction of Delamination in a Bi-material System based on Free-Edge Energy Evaluation", Proceedings of the 53rd IEEE Electronic Components and Technology Conference, May 2003, pp. 1160-1164.

K. Wang et al., "Interfacial Shear Stress, Peeling Stress and Die Cracking Stress in Trilyaer Electronic Assemblies", IEEE 7th Intersociety Conference on Thermomechanical Phenomena in Electronic Systems, May 2000, vol. 2, pp. 56-64.

Y. Luo et al., "An Improved Estimate for Thermal Stresses in Multi-Layer Assemblies", IEEE 11th Intersociety Conference on Thermal and Thermomechanical Phenomena in Electronic Systems, May 2008, pp. 842-852.

T.D. Moore, "Peeling Stress Analyzed for Resistance to Delamination—Application to Multiple Thin Films on a Thick Substrate", IEEE 9th Intersociety Conference on Thermomechanical Phenomena in Electronic Systems, Jun. 2004, vol. 2, pp. 330-335.

University of Southern California, "Graphene Organic Photovoltaics: Flexible Material Only a Few Atoms Thick May Offer Cheap Solar Power", ScienceDaily, Jul. 24, 2010. (retrieved from http://www.sciencedaily.com/releases/2010/07/100723095430.htm).

M. Berger, "Polymer Carpets—A New Class of Nanomaterials for NEMS and MEMS", Nanowerk, Sep. 2, 2010. (retrieved from http://www.nanowerk.com/spotlight/spotid=17875.php).

Massachusetts Institute of Technology, "Funneling Solar Energy: Antenna Made of Carbon Nanotubes Could Make Photovoltaic Cells

(56) References Cited

OTHER PUBLICATIONS

More Efficient", ScienceDaily, Sep. 13, 2010. (retrieved from http://www.sciencedaily.com/releases/2010/09/100912151548.htm).
E. Meng et al., "Polymer MEMS for Micro Fluid Delivery Systems", American Chemical Society (ACS) Polymer MEMS Symposia, New York, New York, USA, Sep. 2003. (two pages).
Extended European Search Report dated Mar. 26, 2012, in European Application No. 11192789.3.
Korean Office Action of Jun. 17, 2013 for Korean Patent Application No. 10-2011-0139346 filed Dec. 21, 2011. 6 pages, 6 page translation.
Notice of Allowance of Dec. 26, 2013 for Korean Patent Application No. 10-2011-0139346 filed Dec. 21, 2011. 2 pages, 1 page translation.
Japanese Office Action of Feb. 26, 2013 for Japanese Patent Application No. 2011279492: filed Dec. 21, 2011. 3 pages, 3 page translation.
Chinese Office Action of Dec. 30, 2013 for Chinese Patent Application No. 201110433902.0, filed Dec. 22, 2011. 6 pages.
Japanese Office Action of Mar. 31, 2014 for Japanese Patent Application No. 2011-279492, filed Dec. 21, 2011. 3 pages, 3 page translation.
Taiwanese Office Action of Jul. 11, 2014 for Taiwanese Patent Application No. 100146568, filed on Dec. 15, 2011. 4 pages, 3 page translation.

\* cited by examiner

100

200

300

400

500

600

700

780

800

820.1

820.2

900

1000

1100

1200

1300

1400

1500

1501

1503

1600

1700

1710

<u>1720</u>

<u>1730</u>

Semiconductor Die 1910

Metal Pads 1920

Scribe Street 1930

Encapsulant (Optional)

1900

Scribe Street 2010

Openings 2020

Final Cut 2030

2000

2100

2200

2300

2400

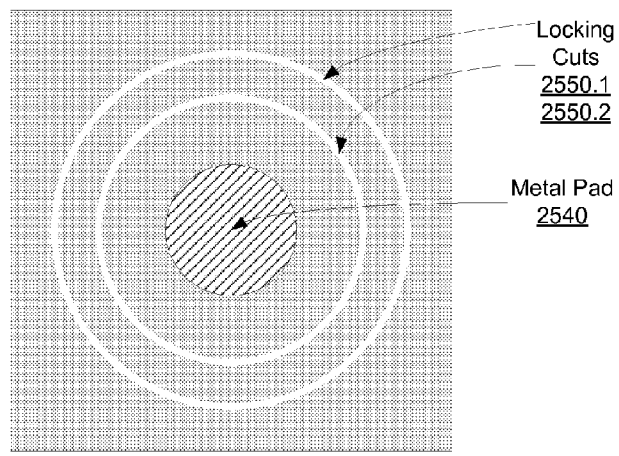
FIG. 25
2500
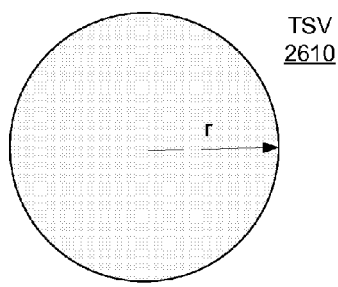
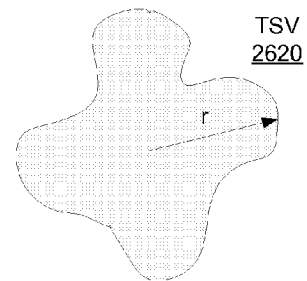
FIG. 26(a)   FIG. 26(b)

2700

2800

2900

3000

3100

3100.1

3200

3300

3300

3500

3600

3700

3800

3900

4000

4001

4100

4200

4300

4400

4500

VERTICALLY INTEGRATED SYSTEMS

RELATED APPLICATIONS

This application is a continuation of U.S. application Ser. No. 12/975,847 filed Dec. 22, 2010, the disclosure of which is incorporated herein by this reference.

BACKGROUND

The present invention relates to integrated circuit systems. In particular, it relates to multi-layer vertically integrated systems with components disposed on a back side of a semiconductor die, away from active components of the die.

Mobile electronic devices such as cellular phones, PDAs, and gaming devices have gained wide popularity recently. Today, these devices have become more of a necessity than a luxury. As a result, electronic devices have been decreasing in size to meet consumer demand for smaller, easier-to-carry devices. Also, the devices have become more complex and offer a multitude of functionalities to the consumer. The different functionalities, however, require more parts in the electronic device and increasing the device size (in the Z axis—as well as the X and Y axes). Consequently, engineers usually must balance the choice of more functionality versus smaller device size. Therefore, engineers constantly are seeking ways to minimize the size of the electrical components that comprise electronic devices.

Electronic devices usually include various integrated circuits that are coupled together on a circuit board. Each integrated circuit performs functions in conjunction with the other integrated circuits in the electronic device. Advances in material sciences have led to decrease in transistor sizes in integrated circuits leading to smaller and more complex electronic devices entering the market place. It would be ideal for electronic devices to provide all circuit systems within integrated circuit chips to minimize space. Unfortunately, modern manufacturing techniques do not provide such capabilities. Accordingly, electronic devices often include a plurality of chips and additional "discrete" devices. Discrete devices are components such as resistors, capacitors, inductors, etc., that are fabricated separately from the semiconductor die. The discrete components are often provided external to the chip but are electrically connected to some circuit within the chip. The discrete component often is mounted on a printed circuit board (PCB) adjacent to the chip, which increases the electronic device size.

Accordingly, there is a need in the art to incorporate discrete passive components in electronic parts without the discrete passive components taking up costly space.

BRIEF DESCRIPTION OF THE DRAWINGS

FIG. 25 illustrates a plan view of an active side according to an embodiment of the present invention.

FIGS. 26(a)-(d) illustrate thru silicon vias according to embodiments of the present invention.

DETAILED DESCRIPTION

Embodiments of the present invention provide an integrated circuit system including a first active layer fabricated on a front side of a semiconductor die and a second pre-fabricated layer on a back side of the semiconductor die and having electrical components embodied therein, wherein the electrical components include at least one discrete passive component. The integrated circuit system also includes at least one electrical path coupling the first active layer and the second pre-fabricated layer.

Embodiments of the present invention provide an electronic device comprising a circuit board and a vertically integrated circuit. The vertically integrated circuit is disposed on the circuit board and comprises a first active layer fabricated on a front side of a semiconductor die; a second pre-fabricated layer on a back side of the semiconductor die and having electrical components embodied therein, wherein the electrical components include at least one discrete passive component; and at least one electrical path coupling the first active layer and the second pre-fabricated layer.

Embodiments of the present invention provide a vertically integrated circuit comprising an active layer having an active circuit, and a component layer disposed on a back side of the active layer, and having a plurality of discrete passive components and links, wherein the discrete passive components are electrically connected to the active circuit.

Figure 1:
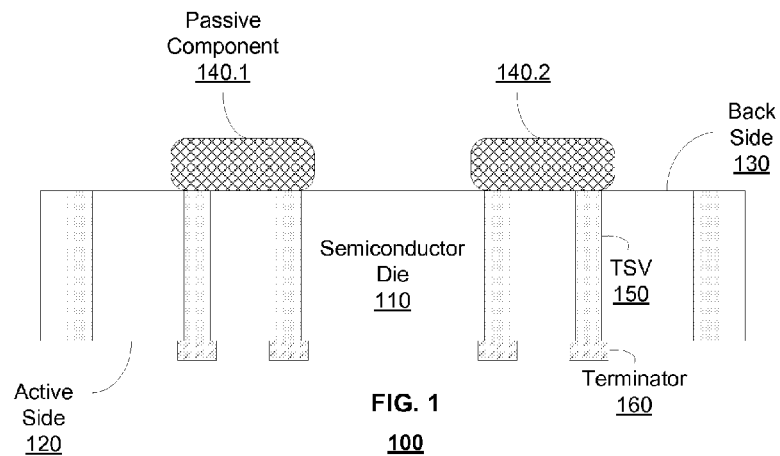
FIG. 1 is a block diagram of an integrated system according to an embodiment of the present invention.

FIG. 1 is a simplified block diagram of an integrated system 100 according to an embodiment of the present invention. The integrated system 100 may include a semiconductor die 110 with two opposed sides, an active side 120 and a back side 130. The integrated system may also include passive components 140.1, 140.2 disposed on the back side 130 that are coupled to the active side 120 by an electrical connector such as a thru silicon via (TSV) 150. The TSV 150 may be coupled to the active side 120 with a terminator 160.

The semiconductor die 110 may be a silicon wafer or other known semiconductor die material. The active side 120 may be located on the front side of the semiconductor die and may include an active circuit that is fabricated thereon during a fabrication process. The active circuit may be etched on to the silicon carrier using known techniques in the art. The active circuit may include semiconductor devices such as transistors that may define functionality of the integrated system 100.

The back side 130 may be located on an opposite side of the semiconductor from the active side 120 on the semiconductor die 110. Passive components 140.1, 140.2 may be mounted directly on the back side 130. The passive components 140.1, 140.2 may be discrete components that may be pre-fabricated separately from the semiconductor die 110 fabrication process. The passive components 140.1, 140.2 may be components that are too big to be made by integrated circuit techniques. The passive components 140.1, 140.2 may be components that do not require an operating power source thus are passive such as resistors, capacitors, and inductors. The passive components 140.1, 140.2 may be comprised of ceramic, silicon, or other suitable materials. FIG. 1 shows two passive components 140.1, 140.2 for illustration purposes only, and embodiments of the present invention may include a different number of passive components of less than or greater than two. For example, an integrated circuit according to the present invention may include one passive component or may include four passive components.

The passive components 140.1, 140.2 may be attached or electrically coupled to the back side 130 of the semiconductor die 110 using a conductive adhesive or paste, anisotropic conductive film or any other suitable method depending on the specific materials involved. The passive components 140.1, 140.2 may also be fabricated using a different fabrication process than for the semiconductor die 110. The passive component fabrication process may be a lower cost fabrication type process as compared to the semiconductor die fabrication process, which may enable passive discrete components with greater performance characteristics to be fabricated than on a finer geometry fabrication process that may be used for more complex structures. The fabricated substrates, the die substrate and the passive component substrate, may be joined using a number of different processes such as gold bonding, glass bonding, anodic bonding or any other suitable bonding method.

TSVs 150 may be vias that are etched or laser-drilled through the semiconductor die 110. After the vias are etched or laser drilled, the vias may then be plated or filled with conductive material to provide an electrical connection between the active side 120 and back side 130. Subsequent processing steps such as bumping or patterning may be provided to make the electrical connection between the TSV 150 and the passive components 140.1, 140.2. The passive components may also be fabricated within or on top of the back side of the silicon (as part of the TSV fabrication process). For example inductive coils or resistors may be fabricated and linked to the TSVs. Also, the TSVs geometries and openings may be modified to facilitate optimum electrical properties of the coupled passive components because different passive components may require different TSV shapes, openings, depths, patterns, etc. For example, an inductive spiral or coil may be fabricated within a TSV. Also, a particular aspect ratio may be required to retain or store charges in a capacitor. So, for example, a recess within the backside of the silicon that is fabricated at the same time as the TSVs may be modified to enhance the electrical properties required. Furthermore, terminators 160 may complete the electrical connection between the TSV 150 and the active circuit on the active side 120. The terminators 160, for example, may be solder bumps and also provide electrical connections to the next packaging level.

In operation, the active circuit on the active side 120 may control the passive components on the back side. The active circuit may access the passive components on the back side 130 as necessary. Therefore, the active circuit may operate as the "brain" of the integrated system 100.

Integrated system 100 may incorporate passive components 140.1, 140.2 on the back side 130 in a vertical manner; therefore, passive components that were previously mounted on the circuit board can now be placed on the back side of semiconductor die thus saving valuable space on the circuit board. Mounting passive components within the semiconductor die may also reduce the vertical height (the Z height) occupied by the vertically integrated system. Also, the use of pre-fabricated components enables different technologies to be mixed. For example, a thin film ceramic substrate that enables passive components such as capacitors may be incorporated into a silicon base die thus producing a single integrated solution.

Figure 2:
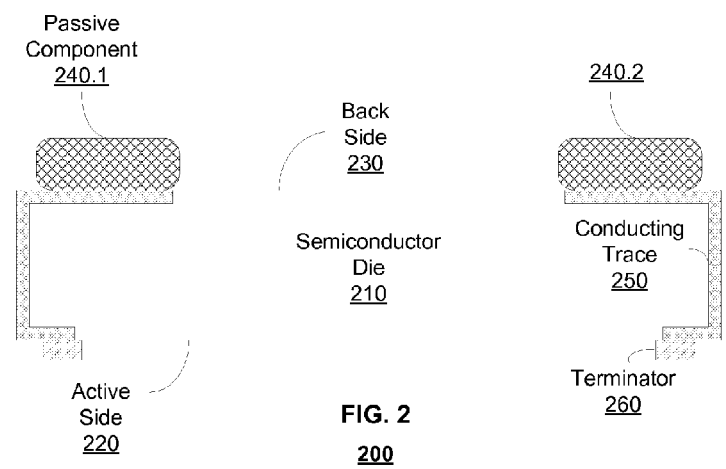
FIG. 2 is a block diagram of an integrated system according to an embodiment of the present invention.

FIG. 2 is a simplified block diagram of an integrated system 200 according to another embodiment of the present invention. The integrated system 200 may include a semiconductor die 210 with two opposed sides, an active side 220 and a back side 230. The integrated system may also include passive components 240.1, 240.2 disposed on the back side 230 that are coupled to the active side 220 by an electrical connector such as a conducting trace 250. The conducting trace 250 may be coupled to the active side 220 with a terminator 260. Also, the conducting trace 250 may run along the side edges of the semiconductor die 210. The integrated system 200 may not require vias to be drilled through the silicon semiconductor die 210 while still incorporating passive components 240.1, 240.2 on the back side 230 in a vertical manner because the conducting trace 250 may couple the two opposing sides along the edges of the semiconductor die.

The other parts of integrated system 200 are similar as those in embodiment shown in integrated system 100 of FIG. 1. Therefore, detailed description thereof will not be repeated here. Moreover, for clarity and brevity, some parts that are common to the above embodiment will not be further shown and described in the following embodiments. For example, terminators to the active side will not be further shown or described because it will be well understood by person of ordinary skill in the art that those are present in the following embodiments.

Figure 3:
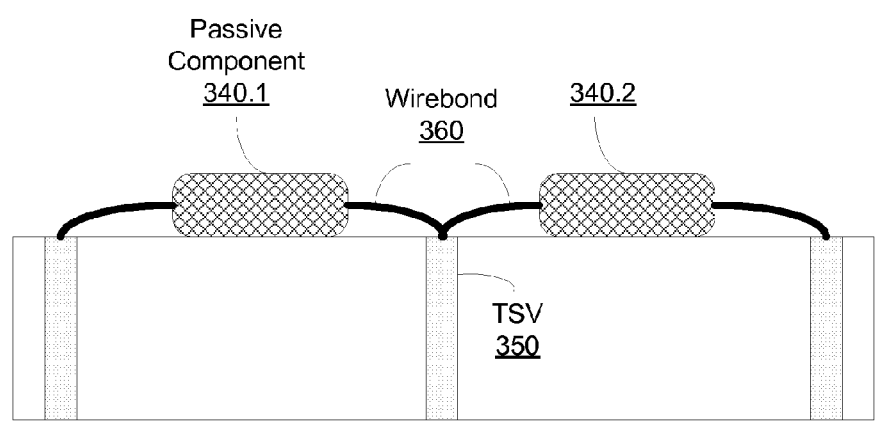
FIG. 3 is a block diagram of an integrated system according to an embodiment of the present invention.

FIG. 3 is a simplified block diagram of an integrated system 300 according to another embodiment of the present invention. The integrated system 300 may include wire bonds 360 that couple passive components 340.1, 340.2 and TSVs 350. Wire bonding may be desired when the passive components 340.1, 340.2 and the semiconductor die are made of different materials with different coefficients of expansion that would lend themselves to standard assembly processes as used for, say, multichip modules (where chip capacitors may be electrically connected using standard wirebonding techniques). If so, the semiconductor die and passive components may expand and contract at different rates in different temperatures leading to cracks in the connections between the two parts. This may be alleviated through the mounted components and wirebonds being encapsulated with an epoxy (or another suitable material) that would protect the relevant joints/interfaces and enable the stresses caused by the thermal coefficient of expansion/material mismatches to be minimized and prevent electrical disconnection through mechanical damage.

Having passive components mounted on the back side of a chip may also allow for more customization in the chip design. The vertically integrated design may provide a chip that may be easily tuned and calibrated to fit a variety of different applications. According to an embodiment of the present invention, an integrated system may be provided that is tunable after assembly of all vertically integrated layers.

Figure 4A:
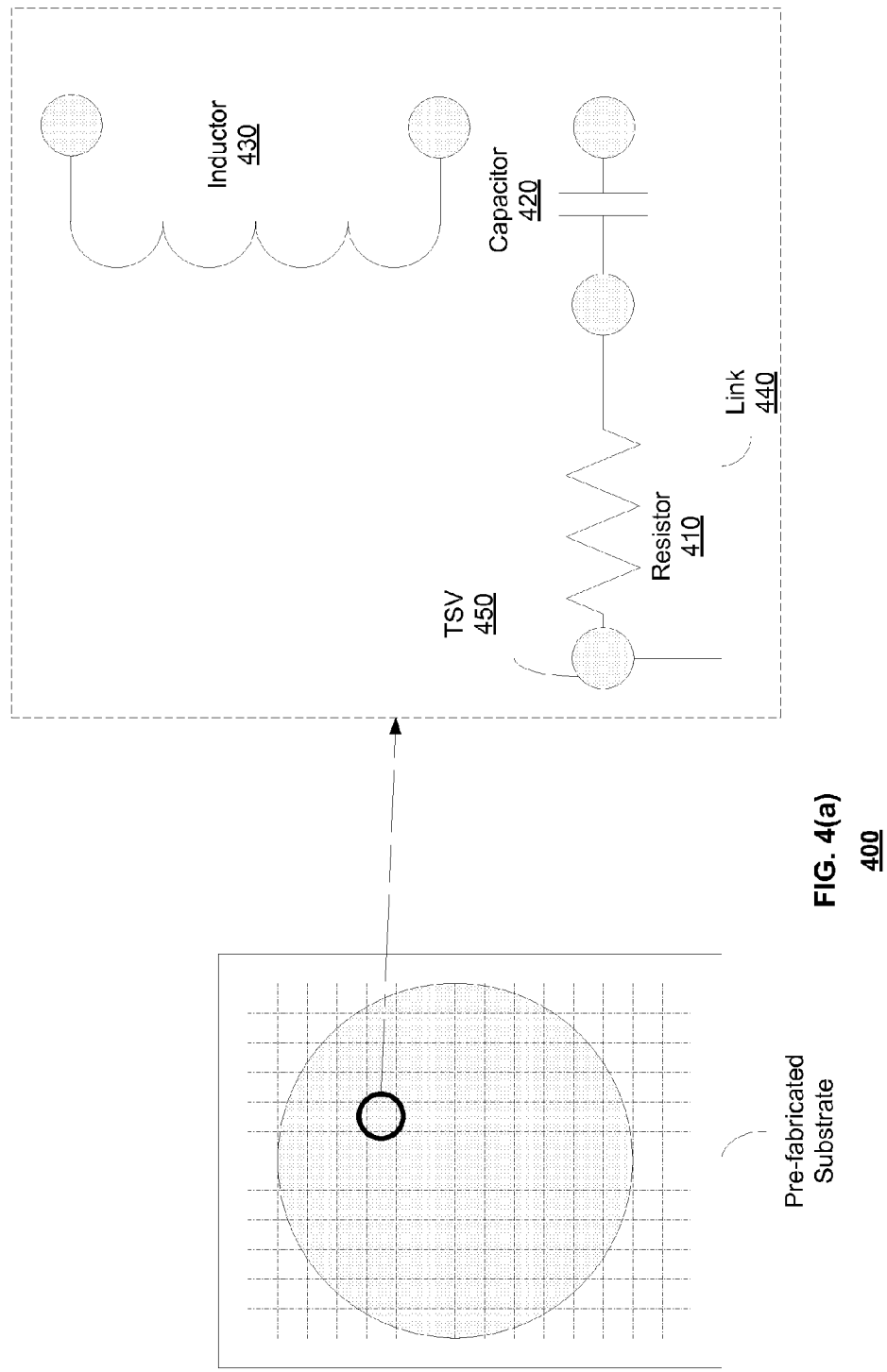
FIG. 4(a) illustrates a component layer according to an embodiment of the present invention.

FIG. 4(a) shows a component layer 400 that may be mounted on the back side of a semiconductor device with passive components such as a resistor 410, a capacitor 420, and an inductor 430, links 440, and TSVs 450. The component layer 400 may be a pre-fabricated substrate such as a thin silicon wafer, ceramic, or glass substrate. For example, the component layer may be a thin silicon wafer that is six, eight, or 12 inches in material. The component layer 400 may be a silicon substrate, ceramic substrate, or a printed circuit board (PCB) type substrate, and may be pre-fabricated at a different site than the active silicon carrier. Furthermore, the pre-fabricated substrate may be made by sputtering, plating, or depositing structures on the base silicon. If the component layer 400 is a separate pre-fabricated layer, it may be joined to the active layer (carrier silicon) using, for example, anodic bonding, gold bonding, anisotropic conductive film or another suitable method.

The component layer 400, for example, may be manufactured on silicon using a less complex process than that used for the carrier silicon. The different silicon substrates may ease the fabrication of some passive component performance characteristics. For example, the component layer 400 may have a thinner geometry than compared to the carrier silicon die. The incorporation of the passive components onto or within the component layer 400 may be further optimized depending on the performance characteristics required. For example, if fabricating a capacitor, the depth and surface area of the two parallel plates deliver a better capacity to store charge. This may be reflected in different shapes/combinations used to maximize the area of the parallel plates as described below in the descriptions of FIGS. 8(b) and 8(c).

Different manufacturing processes may be mixed together to maximize desired performance characteristics of a specific passive component. The component layer 400 may be electrically connected to the carrier silicon, and the component layer 400 may include links to the passive components incorporated therein. The links may be capable of being broken or modified such that the performance characteristics of the passive components incorporated therein are modified. Thus, the integrated system may be tunable after singulation.

As shown further in blow out portion FIG. 4(a), the component layer 400 may include basic building block arrays of passive components. The component layer 400 may include passive components such as resistor 410, capacitor 420, and inductor 430. For illustration purposes, FIG. 4(a) shows the passive components as their respective circuit schematic symbols. The arrays of passive components in component layer 400 may be modified such that the specific number and type of passive components that are electrically connected to the carrier silicon below (for example, through electrically blowing fused links or laser trimming) are set when the whole system is electrically connected (before singulation). Therefore, the whole vertically integrated system may be tuned or calibrated.

Figure 4B:
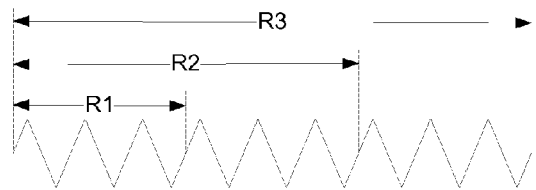
FIG. 4(b) illustrates resistor tuning according to an embodiment of the present invention.

The passive components may be modifiable or tunable for specific applications. FIGS. 4(b)-(e) illustrate different techniques that may be used to tune passive components. FIG. 4(b) shows a resistor component in schematic symbol form that may have a total resistance value of R3. In this example, the resistance may depend directly on the resistor's length. Thus, the resistor may be laser-trimmed to produce a smaller resistance value. For example, the resistor may be trimmed to produce smaller resistances R2 and R1 as shown. Alternatively, the width of the passive component may be modified as the length remains constant such that the resistance may directly depend on the passive component's width. The modification may be carried out by laser trimming, physical modification of relevant links or structures, or other suitable techniques.

Figure 4C:
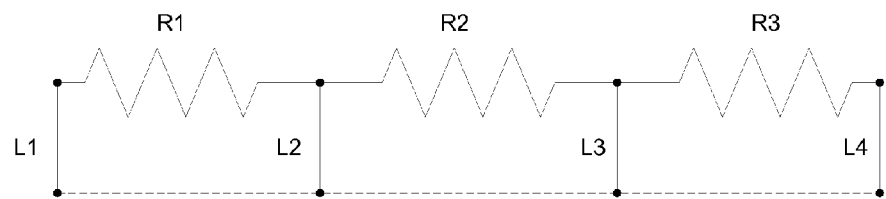
FIG. 4(c) illustrates resistor tuning according to an embodiment of the present invention.

FIG. 4(c) shows another method of tuning a resistance value. In this example, three resistors, R1, R2, and R3, may be coupled in series. Different links, L1, L2, L3 and L4, also may be provided in between the resistors' connections. Depending on which resistance value is preferable, the links may be selectively fused or broken. For example, if resistance value of R2 is preferable, links L1 and L4 may be broken thus leaving only links L2 and L3 that are coupled to each end of resistor R2. In another example, if resistance value of R1+R2 is preferable, links L2 and L4 may be broken thus leaving only links L1 and L3 that provide R1 and R2 in series. Moreover, the resistors may be arranged in a parallel fashion with the links arranged accordingly. Alternatively, the different links L1, L2, L3 and L4 may be connected together on a common track, which may be subsequently modified to break or modify connections as designed.

Figure 4D:
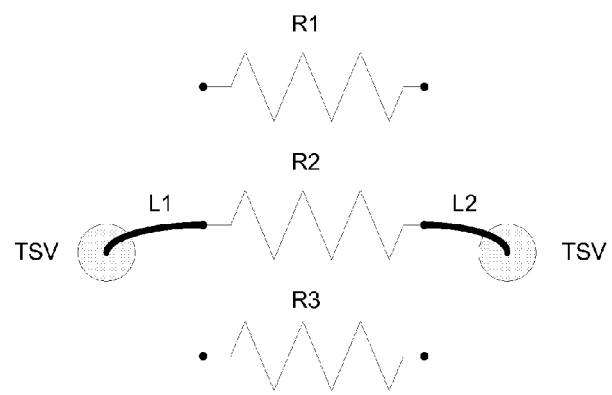
FIG. 4(d) illustrates resistor tuning according to an embodiment of the present invention.

FIG. 4(d) shows another method of tuning a resistance value. In this example, three resistors may be provided so that each of the resistors may be coupled to the TSVs. Depending on which resistance value is preferable, the resistors may be selectively coupled to the TSVs through wire bonding. In another embodiment, all resistors may be coupled to the TSV and, subsequently, bonds to all but one resistor may be broken. Also, electrical structures within layers of the vertically integrated system may be connected through fused links, which can be electrically blown in order to tune the system.

Figure 4E:
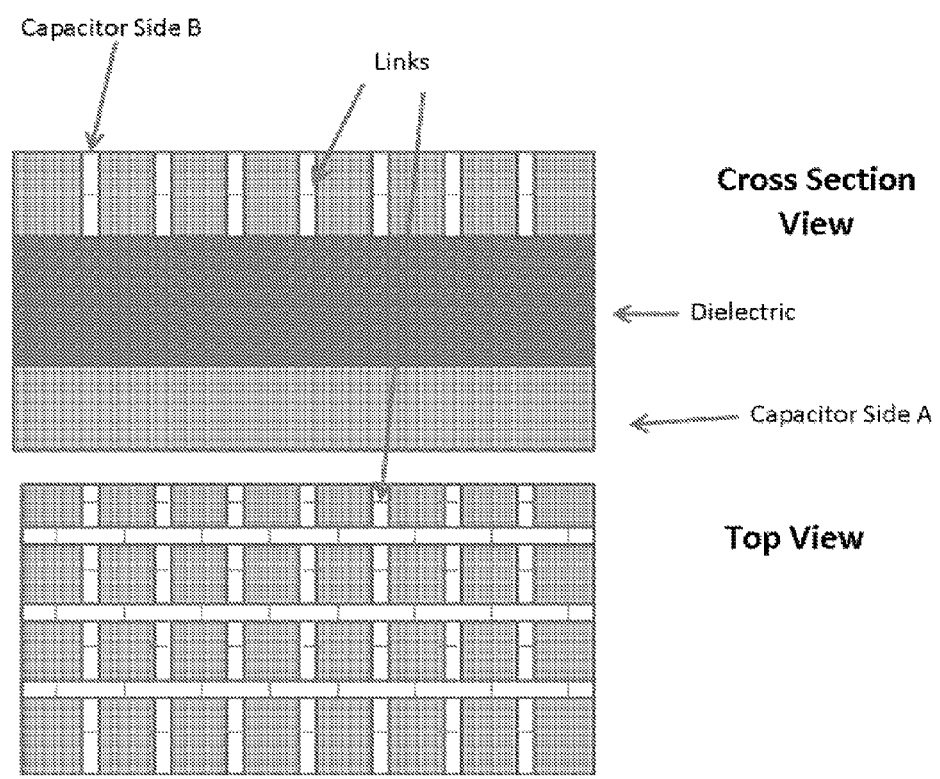
FIG. 4(e) illustrates capacitor tuning according to an embodiment of the present invention.

FIG. 4(e) illustrates a method of tuning a capacitance value. FIG. 4(e) shows a cross section view and a top view of a passive discrete capacitor. The capacitor may have two parallel sides, A and B, that store charge, and the two parallel sides may be separated by a dielectric. One side of the capacitor may include electrical links that may be modifiable. For example, the links may be broken reducing the size of the capacitor plates and, thus, reducing the capacitance.

In the case of an inductor, the properties may be influenced by the number of turns in the inductor coil. Links between layers, which contain different numbers of turns, may be modified by blowing fuses that connect the turns on each layer. Multiple turns and links may be connected on each layer and these links may be fused (and then blown electrically) or physically modified.

Moreover, component layer 400 may also include links 440 between the passive components and TSVs 450 that electrically connect to the active layer underneath. Consequently, the links 400 may be broken or altered to also tune or modify the integrated system. As a result, the integrated system as a complete stack may be electrically tested and the components in the component layer on the back side may be tuned, modified, or calibrated subsequently. Since the vertically integrated system allows tuning, modification, or calibration in wafer sandwich form after assembly of all layers, the vertically integrated system is easily customizable for different applications. Also, different individual systems can be singulated after a complete stack is assembled, electrically tested, and tuned leading to easy incorporation into the next packaging level on (or within) the circuit board.

Figure 5:
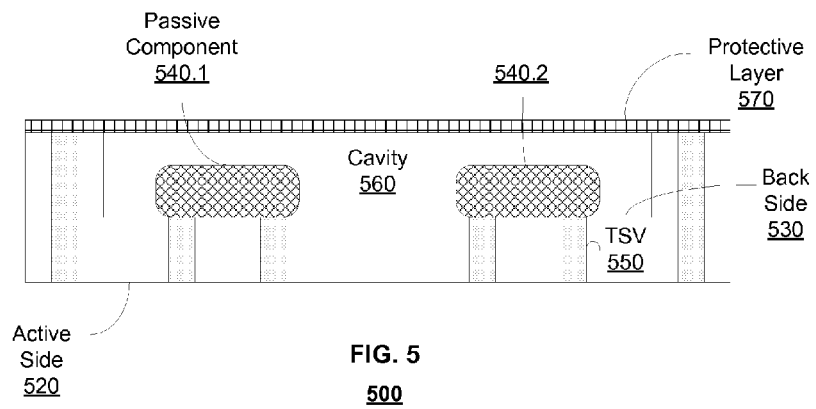
FIG. 5 is a block diagram of an integrated system according to an embodiment of the present invention.

FIG. 5 is a simplified block diagram of an integrated system 500 according to another embodiment of the present invention. The integrated system 500 may include a semiconductor die with an active side 520 and a back side 530 that incorporates passive components 540.1, 540.2. TSVs 550 may couple the passive components 540.1, 540.2 to an active circuit on the active side 520. The integrated system may include a cavity 560 on the back side 530 in where the passive components 540.1, 540.2 are mounted. Also, the integrated system 500 may include a protective layer 570.

Cavity 560 may be recess etched into the back side or formed within the back side of the semiconductor die. By having the passive components 540.1, 540.2 mounted within the cavity, the overall system height of the vertically integrated system is greatly reduced leading to further reduction in component size.

Protective layer 570 may be coupled to the layers below such as the active side 520 by vias and may offer protective covering to the passive components 540.1, 540.2. The protective layer 570 may be an electromagnetic field (EMF) shielding. Also, the protective layer 570 may include a ground plane or a power plane for the integrated system 500. Since the protective layer 570 is on top of the other layers, the protective layer 570 may dissipate heat produced by the layers below. The protective layer 570 may also contain passive components. Therefore, the protective layer 570 may provide EMF shielding and provide an additional component layer at the same time. Also, protective layer 570 may be modifiable to tune or calibrate the integrated system 500, for example when all the layers are assembled together before singulation. The protective layer 570 may be modifiable electrically through laser trimming, blowing fuses, or other known techniques.

Figure 6:
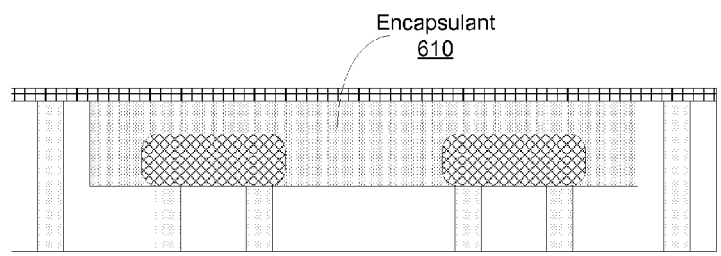
FIG. 6 is a block diagram of an integrated system according to an embodiment of the present invention.

FIG. 6 is a simplified block diagram of an integrated system 600 according to another embodiment of the present invention that is similar to integrated system 500 of FIG. 5. Integrated system 600 may include an encapsulant 610 that fills the cavity. The encapsulant 610 when hardened may mold around the passive components locking them in place.

Figure 7A:
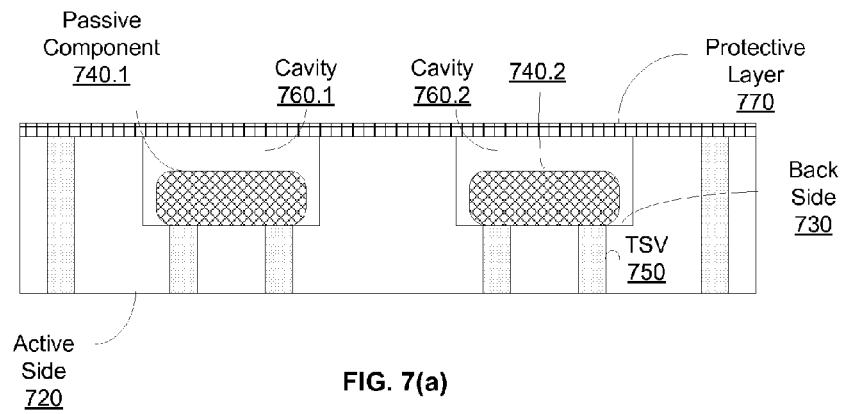
FIG. 7(a) is a block diagram of an integrated system according to an embodiment of the present invention.
Figure 7B:
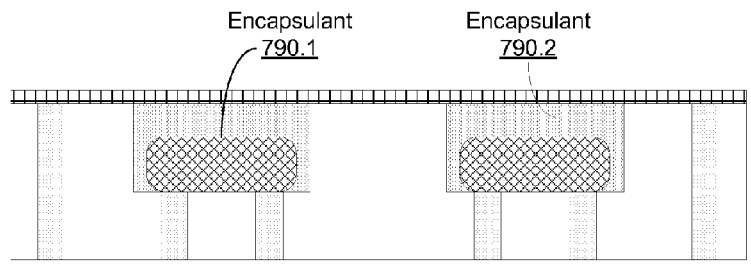
FIG. 7(b) is a block diagram of an integrated system according to an embodiment of the present invention.

According to another embodiment of the present invention, the integrated system may include multiple cavities. Integrated system 700 in FIG. 7(*a*) may include two cavities 760.1, 760.2 where a passive component 740.1, 740.2 may be mounted in each cavity respectively. Also, each cavity may have more than one passive component mounted therein. FIG. 7(*b*) shows an integrated system 780 that may include multiple cavities with an encapsulant 790.1, 790.2 that fills the cavities respectively. The encapsulant 790.1, 790.2, when hardened, may mold around the passive components locking them in place.

Figure 8A:
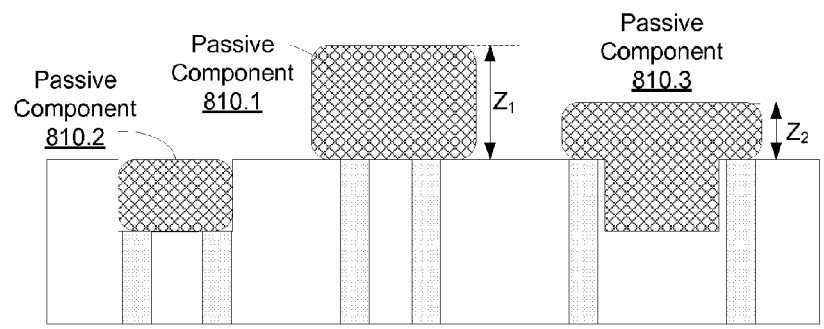
FIG. 8(a) is a block diagram of an integrated system according to an embodiment of the present invention.
Figure 8B:
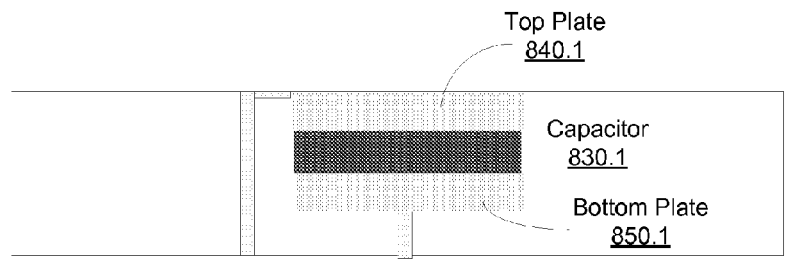
FIG. 8(b) is a block diagram of an integrated system according to an embodiment of the present invention.
Figure 8C:
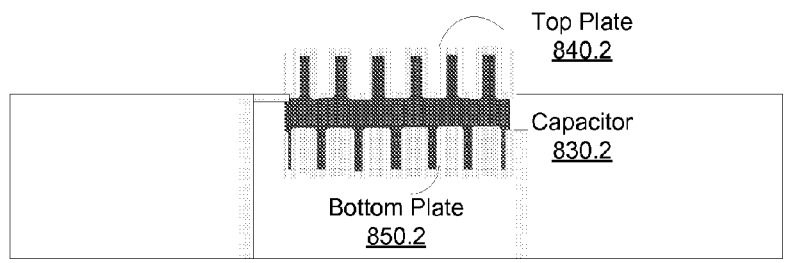
FIG. 8(c) is a block diagram of an integrated system according to an embodiment of the present invention.

Passive components may be mounted or embedded within the semiconductor die in different manners depending on the size of the passive component and the electrical properties of the passive component. FIG. 8(*a*) illustrates three passive component devices mounted in different manners on the back side of a semiconductor die according to an embodiment of the present invention. Passive component 810.1 may be mounted directly onto the back side with no cavity and having a vertical height of $Z_1$. On the other hand, passive component 810.2 may be mounted entirely within a cavity where filling the depth and width of the cavity may improve the electrical properties of the passive component 810.2. For example, increasing the depth of the cavity may allow more resistive material to be incorporated into the cavity and, thus, increasing the overall resistance properties.

Embedding the passive component 810.2 entirely within the cavity reduces the vertical height of the integrated system because the passive component 810.2 does not add a z height of its own. Passive component 810.3 may be mounted on the back side such that it fills a cavity and also overlaps the cavity. The total volume achieved by filling the depth and width of the cavity and the additional overlap may improve the electrical properties of the passive component 810.3. For example, overlapping material around a cavity may increase the total volume of the resistive material and, thus, may increase the overall resistance properties. Furthermore, $Z_2$, the z height of the passive component 810.3, is less than $Z_1$, which is the vertical height of the passive component 810.1 that is mounted directly on the back side. Therefore, the vertical height of the system may be reduced by employing different mounting techniques described herein.

The cavity or recess, into which the passive component is mounted, may be shaped and modified to optimize the performance required. For example, FIG. 8(*b*) shows an integrated system 820.1 with a capacitor 830.1 as a passive component mounted on the back side within a cavity entirely according to an embodiment of the present invention. The cavity and the TSVs are shaped so that the top plate 840.1 and bottom plate 850.1 of the capacitor 830.1 fit the cavity. Moreover, the cavity may be further modified to allow for higher valued capacitors to be used. FIG. 8(*c*) shows an integrated system 820.2 with a capacitor 830.2 as a passive component mounted on the backside in a cavity according to an embodiment of the present invention. The cavity in this embodiment may be stepped to maximize the surface area of the parallel plates, the top plate 840.2 and bottom plate 840.3 of the capacitor 830.2. Since the capacitance is directly related to the surface area of the parallel plates, the capacitance increases and, thus, the amount of charge stored increases.

Figure 9:
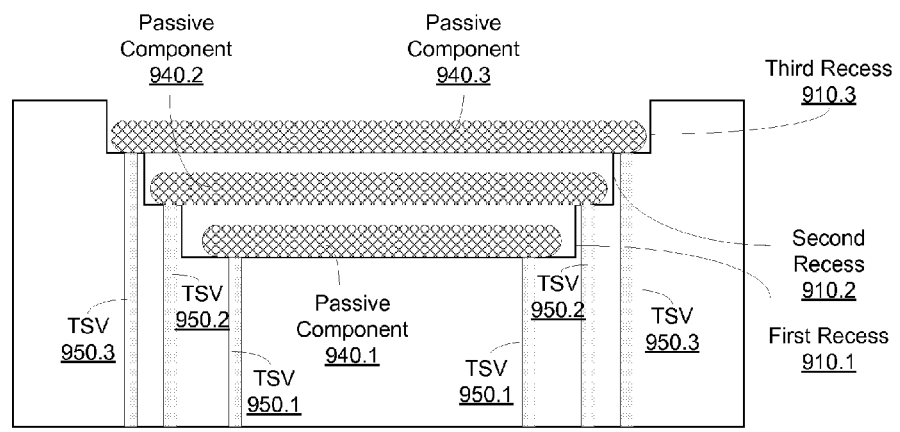
FIG. 9 is a block diagram of an integrated system according to an embodiment of the present invention.

FIG. 9 is a simplified block diagram of an integrated system 900 according to another embodiment of the present invention. Integrated system 900 may include multiple passive components stacked on top of each other with each passive component being mounted in respective recess. First recess 910.1 may have passive component 940.1 mounted therein; second recess 910.2 may have passive component 940.2 mounted therein; and third recess 910.3 may have passive component 940.3 mounted therein. Each passive component may be electrically connected to an active circuit on the active side by TSVs as shown in FIG. 9. The passive component 940.1 may be connected to the active circuit by the pair of TSVs 950.1, the passive component 940.2 may be connected to the active circuit by the pair of TSVs 950.2, and the passive component 940.3 may be connected to the active circuit by the pair of TSVs 950.3. Each recess may be etched into the back side or formed within the back side of the semiconductor die with a stepped profile. The "stepping" of the recesses or cavities within the back side of the semiconductor die may enable many different passive components to be incorporated into the integrated system 900 while minimizing both the horizontal length and vertical height of the integrated system 900. The passive components 940.1, 940.2, 940.3 may be pre-fabricated together on substrates yet still separate from the semiconductor die. The pre-fabricated substrates may then be inserted into the stepped recesses of the semiconductor die for assembly.

Figure 10:
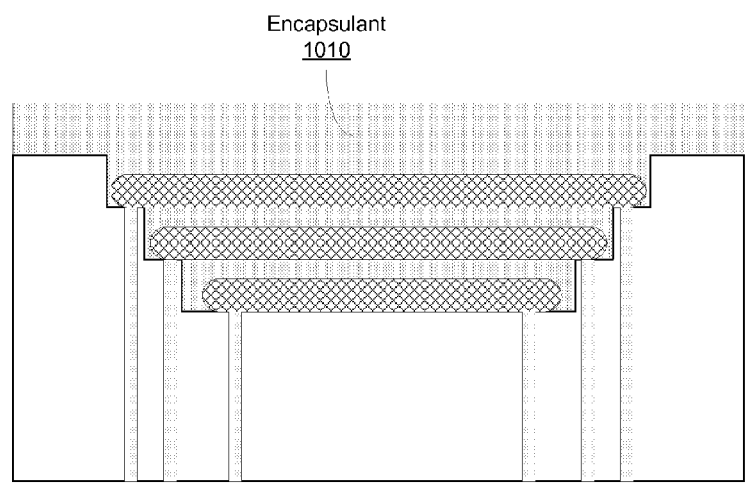
FIG. 10 is a block diagram of an integrated system according to an embodiment of the present invention.

FIG. 10 is a simplified block diagram of an integrated system 1000 according to another embodiment of the present invention that is similar to integrated system 900 of FIG. 900. Integrated system 1000 may include an encapsulant 1010 that fills the cavity. The encapsulant 1010 when hardened may mold around the passive components in each recess locking them in place.

Figure 11:
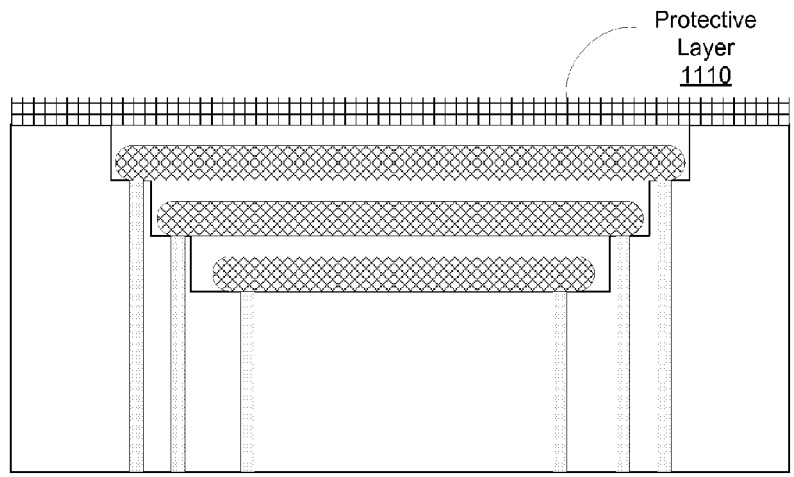
FIG. 11 is a block diagram of an integrated system according to an embodiment of the present invention.
Figure 12A:
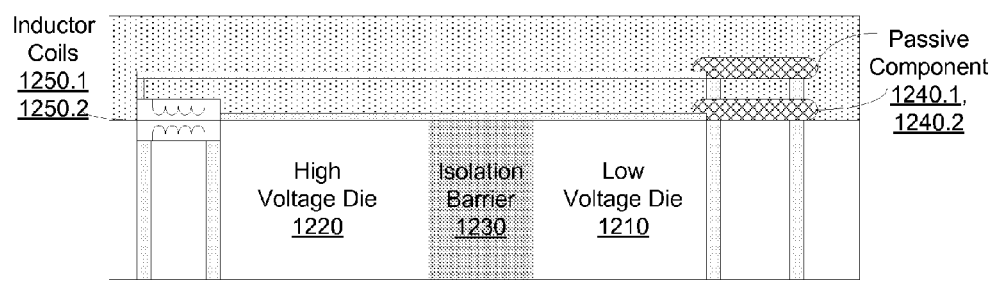
FIG. 12(a) is a block diagram of an integrated system according to an embodiment of the present invention.
Figure 12B:
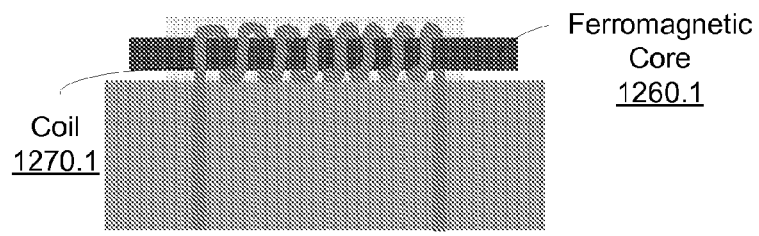
FIGS. 12(b)-(d) are block diagrams of integrated systems including an inductor according to embodiments of the present invention.
Figure 12C:
Figure 12D:
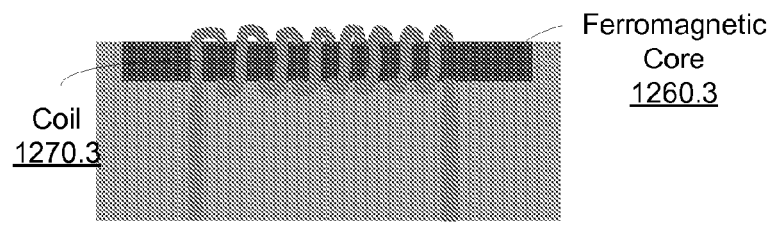
Figure 12E:
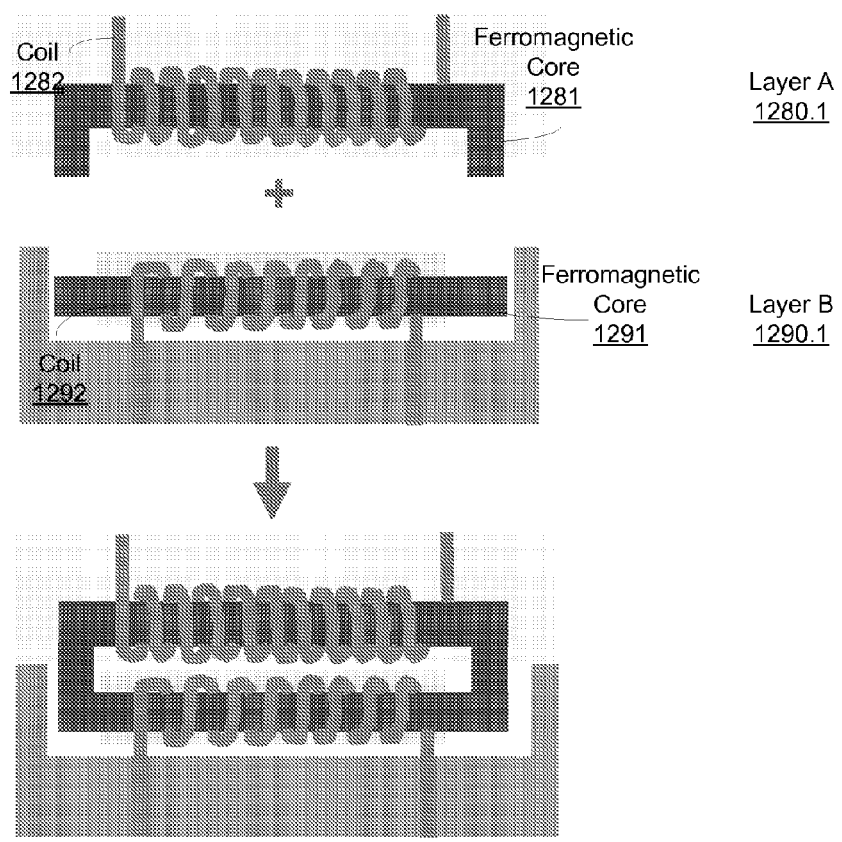
FIGS. 12(e)-(f) are block diagrams of integrated systems including transformers according to embodiments of the present invention.
Figure 12F:
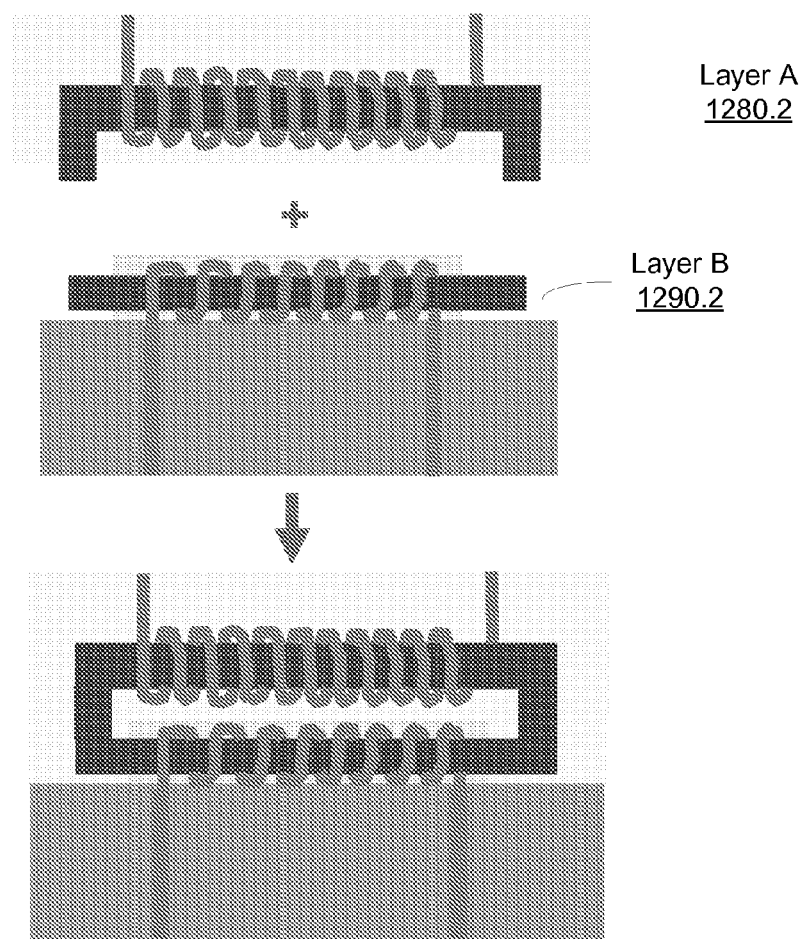

Moreover, a protective layer 1110 as shown in FIG. 11 may be placed on top of the passive components. Protective layer 1110 may be coupled to the layers below such as the active side by vias and may offer protective covering to the passive components. The protective layer 1110 may be an electromagnetic field (EMF) shielding. Also, the protective layer 1110 may include a ground plane or a power plane for the integrated system 1100. Since the protective layer 1110 is on top of the other layers, the protective layer 1110 may dissipate heat produced by the layers below. The protective layer 1110 may also contain passive components. Therefore, the protective layer 1110 may provide EMF shielding and provide an additional component layer at the same time. Also, the protective layer 1110 may be modifiable to tune or calibrate the integrated system 1100, for example, when all the layers are assembled together before singulation. The protective layer 1110 may be modifiable electrically through laser trimming, blowing fuses, or other known techniques.

FIG. 12(*a*) is a simplified block diagram of an integrated system 1200 according to another embodiment of the present invention. Integrated system 1200 may use inductor coils placed on the back side to isolate and couple electrical signals from dies of different voltage domains. Integrated system 1200 may include a low voltage die 1210 and a high voltage die 1220 separated by an isolation barrier 1230. The integrated system also may include passive components 1240.1, 1240.2, and a pair of inductor coils 1250.1, 1250.2.

The low voltage die 1210 and high voltage die 1220 operate on different voltage domains that are electrically separated. Isolation barrier 1230 may electrically separate the two dies and may be made of a non-conducting material. The passive components 1240.1, 1240.2 may be incorporated into (or deposited on top of) the back side and may be directly coupled to an active circuit of the low voltage die 1210. The passive components 1240.1, 1240.2 may also be coupled to one of the inductor coils 1250.1, 1250.2 while the other coil may be coupled to an active circuit of the high voltage die 1220. Consequently, integrated system 1200 may use the inductor coils 1250.1, 1250.2 to isolate and magnetically couple electrical signals between the two dies, low voltage die 1210 and high voltage die 1220, through the pre-fabricated substrate including passive components 1240.1, 1240.2. The pre-fabricated substrate layer may also contain a protective layer as described above.

Ferromagnetic materials may also be included within the coils. FIG. 12(*b*) is a simplified block diagram of an inductor incorporated into an integrated system according to an embodiment of the present invention. The inductor may have a ferromagnetic core 1260.1 and a coil 1270.1 wrapped around the ferromagnetic core 1260.1. The inductor may be pre-fabricated and mounted onto the back side of the semiconductor die. Also, the inductor may be connected to the active side with conductive paths such as a TSV.

FIG. 12(*c*) is a simplified block diagram of an inductor into an integrated system according to an embodiment of the present invention. The inductor may have a ferromagnetic core 1260.2 and a coil 1270.2 wrapped around the ferromagnetic core 1260.2. In this embodiment, the inductor may be pre-fabricated and inserted within a cavity on the back side of semiconductor die. Also, the inductor may be connected to the active side with conductive paths such as a TSV.

FIG. 12(*d*) is a simplified block diagram of an inductor into an integrated system according to an embodiment of the present invention. The inductor may have a ferromagnetic core 1260.3 and a coil 1270.3 wrapped around the ferromagnetic core 1260.3. In this embodiment, the inductor may be fabricated within the back side of semiconductor die. Also, the inductor may be connected to the active side with conductive paths such as a TSV.

The ferromagnetic materials may be used to form transformers within the layers of the integrated system. The transformer may be a step up or step down transformer. For example, a transformer formed within the layers may be used as an RF transformer. FIG. 12(*e*) illustrates a transformer forming method according to an embodiment of the present invention. A pre-fabricated layer A 1280.1 may contain a coil 1282 wrapped around a ferromagnetic core 1281. The layer A 1280.1 may be a fabricated PCB, ceramic, or other suitable substrate. The layer A 1280.1 may also contain other passive components, shielding, power plane, and ground planes. The layer A 1280.1 may also contain connections to other layers. Another layer B 1290.1 may be the back side of the semiconductor die. The layer B 1290.1 may contain a coil 1292 wrapped around a ferromagnetic core 1291 that is mounted within a cavity in the semiconductor die back side. The two layers, layer A 1280.1 and layer B 1290.1, may be joined and the ferromagnetic cores 1281, 1291 of each respective layer may connected to form a transformer with coil 1281 being a top coil and coil 1282 being a bottom coil of the transformer. Moreover, an encapsulant may fill the cavity. Alternatively, the transformer may be mounted directly onto the back side of the semiconductor die.

FIG. 12(*f*) illustrates a transformer forming method according to an embodiment of the present invention. The transformer in FIG. 12(*f*) may contain a pair of coils wrapped around a ferromagnetic core as shown. The transformer may be formed on a substrate that is mounted with a thick dielectric onto the back side of the die. The dielectric may deform and heat and pressure, leaving the core endings exposed that may be mounted on the back side of the die.

Figure 13:
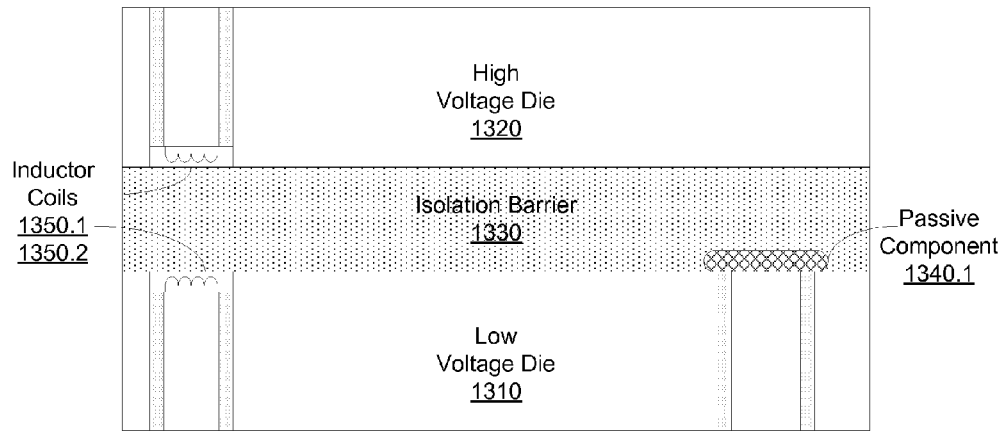
FIG. 13 is a block diagram of an integrated system according to an embodiment of the present invention.

FIG. 13 is a simplified block diagram of an integrated system 1300 according to another embodiment of the present invention. Integrated system 1300 also may use inductor coils placed on the back side to isolate and couple electrical signals to and from different voltage dies that cannot be directly coupled similar to the integrated system 1200 of FIG. 12(*a*); however, in integrated system 1300 the substrate that includes the passive component is also used as an isolation circuit between the differing voltage dies. Integrated system 1300 may include a low voltage die 1310, a high voltage die 1320, an isolation barrier 1330, passive component 1340.1 and a pair of inductor coils 1350.1, 1350.2. In this embodiment, the high voltage die 1320 may be stacked on top of the low voltage die 1310 with the isolation barrier 1330 in between the two dies to electrically isolate the two dies. The isolation circuit may be a pre-fabricated substrate as described in the present invention that includes passive components.

In another aspect of integrated system 1300, the active circuit in the low voltage die 1310 may control operations of the other layers including the passive component 1340.1 and high voltage die 1320 circuits. The low voltage die 1310 may access the other layers.

Figure 14:
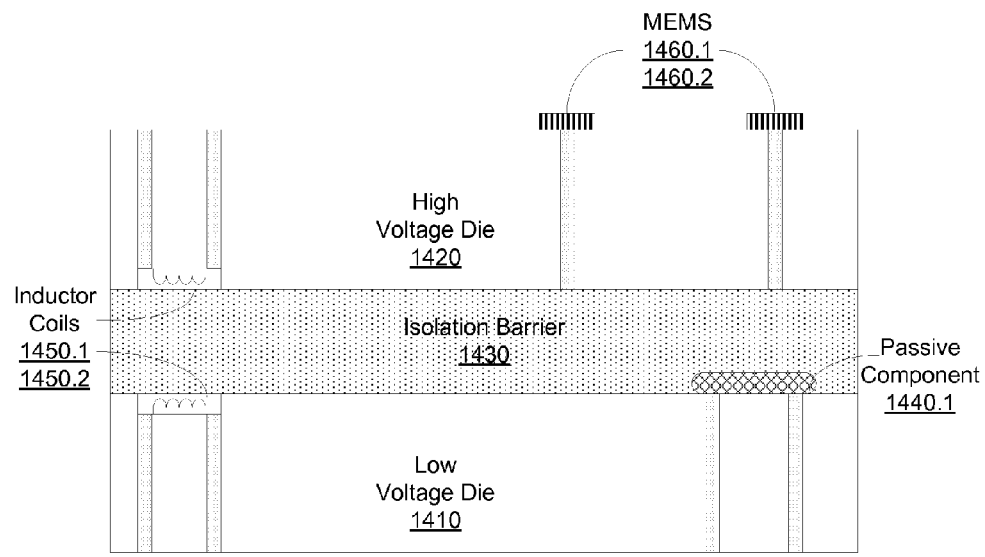
FIG. 14 is a block diagram of an integrated system according to an embodiment of the present invention.

FIG. 14 is a simplified block diagram of an integrated system 1400 according to another embodiment of the present invention that is similar to integrated system 1300 of FIG. 1300. Integrated system 1400 may further include microelectromechanical systems (MEMS) 1460.1, 1460.2 on the high voltage die 1420. For example, the low voltage die 1410 may contain a memory portion that stores a mechanical position for the MEMS 1460.1, 1460.2 such as an initial position for a gyroscope. When the integrated system 1400 is in operation, the sensitivity and output of the MEMS may be normalized to an initial mechanical position. Other application examples may include RF MEMS switches, arranged in series or parallel, for antenna tuning in different frequency bands.

The isolation barrier 1430 may also contain ferromagnetic materials positioned between the coils. The ferromagnetic materials may deliver a step up or step down transformer as required within the integrated system.

Figure 15A:
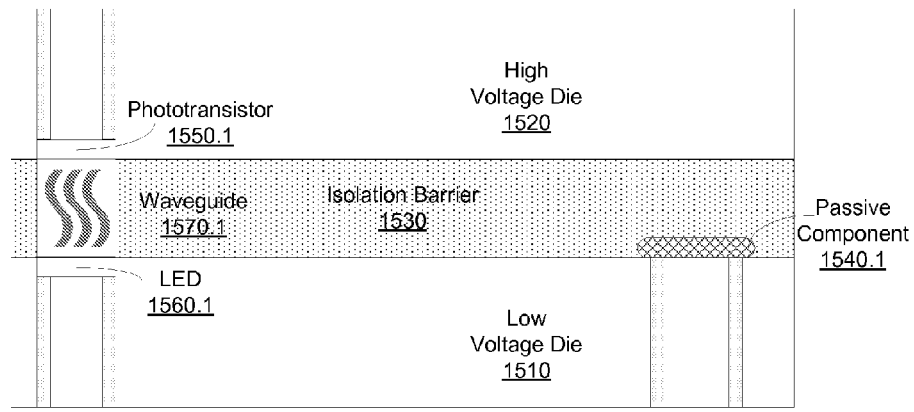
FIG. 15(a) is a block diagram of an integrated system according to an embodiment of the present invention.

According to another embodiment of the present invention, an optics system may isolate and couple electrical signals from different dies that operate in different isolated domains. FIG. 15(*a*) is a simplified block diagram of an integrated system 1500 that includes an optics system. The integrated system 1500 may include may include a low voltage die 1510, a high voltage die 1520, an isolation barrier 1530, and a passive component 1540.1. The integrated system 1500 may also include an optics system with a phototransistor 1550, an LED 1560.1, and a waveguide 1570. In this embodiment, the high voltage die 1520 may be stacked on top of the low voltage die 1510 with the isolation barrier 1530 in between the two dies to electrically isolate the two dies. The isolation circuit may be a pre-fabricated substrate as described above that includes passive components.

In this embodiment, the optics system may isolate and optically couple the electrical signals between two differing operating voltage dies, 1510 and 1520. A phototransistor 1550.1 may be placed on one of the dies, for example the high voltage die, and a corresponding LED 1560.1 may be placed on the other die. A waveguide 1570.1 may also be placed in between the phototransistor 1550.1 and LED 1560.1 in order for optic waves to be able to travel. The waveguide 1570 may be formed within the isolation barrier 1530. In operation, the active circuit on the low voltage die 1510 may turn on the LED 1560.1, on one end of the waveguide 1570.1, as a communication signal. The phototransistor 1550.1, at the other end of the waveguide 1570.1, will sense when the LED 1560.1 is turned "ON" and transmit the information to the circuit on the high voltage die 1520 circuits. Consequently, the active circuit in the low voltage die 1510 may control operations of the other layers including the passive component 1540.1 and high voltage die 1520 circuits. The low voltage die 1510 may access the other layers as necessary.

Figure 15B:
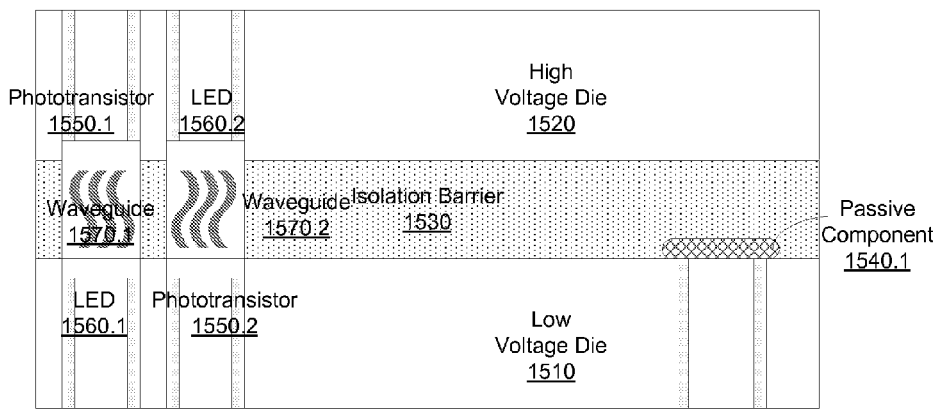
FIG. 15(b) is a block diagram of an integrated system according to an embodiment of the present invention.

Alternatively, the optic system may be a bi-directional communication system between layers as shown in FIG. 15(b) according to an embodiment of the present invention. In a bi-directional communication system, each die may include a phototransistor 1550.1, 1550.2 and an LED 1560.1, 1560.2 allowing communication in both directions.

Figure 15C:
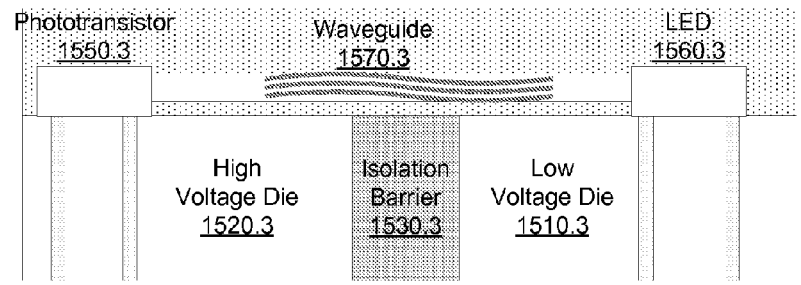
FIG. 15(c) is a block diagram of an integrated system according to an embodiment of the present invention.

Furthermore, an optic system may be used when the two dies are placed side by side on a layer. FIG. 15(c) is a simplified block diagram of an integrated system 1503 according to an embodiment of the present invention. The low voltage die 1510.3 and high voltage die 1520.3 may be on a same layer and may be separated by isolation barrier 1530.3. An optic system may be mounted on the two dies. The optics system may include a phototransistor 1550.3, an LED 1560.3, and a waveguide 1570.3.

Figure 16:
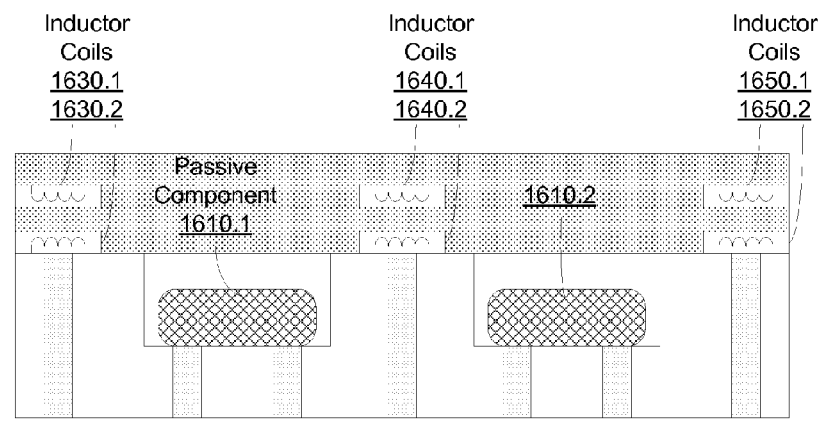
FIG. 16 is a block diagram of an integrated system according to an embodiment of the present invention.

Integrated system 1600 of FIG. 16 shows an embodiment according to the present invention of how the active circuit on the active side can access different passive components. Integrated system 1600 may include passive components 1610.1, 1610.2 and inductor coils 1630-1650 placed in a top substrate that is coupled to passive components and the active circuit. The inductor coils 1630-1650 may switch on/off to activate/deactivate the passive components 1610.1, 1610.2. For example, the active circuit may send a voltage to inductor coils 1630.1, 1630.2 when it needs to access passive component 1610.1. A pair of inductor coils may also control access to a block of passive components and not just one passive component.

The integration of different layers/materials on the back side of a semiconductor die may lead to structural instability. The adhesion between the different layers may be crucial to keep structural integrity (during the operation/lifetime of the vertically integrated system and also during the singulation of the individual vertically integrated systems). Coefficients of thermal expansion (CTE) between dissimilar material layers in a multi-layer system generate stresses which are concentrated on the edges. In other words, stresses that can lead to shearing and peeling of the bonds between layers are strongest on the edges, which can be exacerbated when a multi-layer system contains many thin layers of different materials. Therefore, according to the present invention, different embodiments described below are provided that maximize adhesion at the edge of the embedded component and, therefore, improve the mechanical robustness of the vertically integrated system.

Figure 17A:
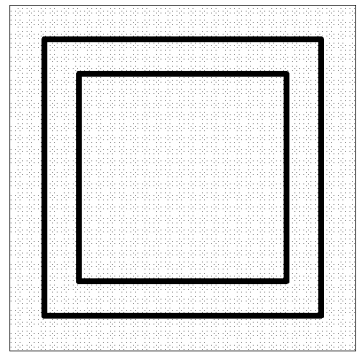
FIG. 17(a) illustrates a plan view and cross section view of an integrated system according to an embodiment of the present invention.
Figure 17A:
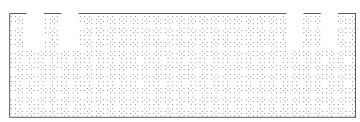

FIG. 17(a) shows an integrated system 1700 according to an embodiment of the present invention. Integrated system 1700 may include tracks in the semiconductor die perimeter. The top section of FIG. 17(a) shows a plan view of the die with two tracks, and the bottom section shows a cross section view with the two tracks. The tracks may be formed on the back side of the semiconductor die with laser cuts or by an etching or some other process capable of providing the required deformation. The tracks form ridges for an encapsulant to be embedded within thus more securely attaching the multiple layers to each other.

Figure 17B:
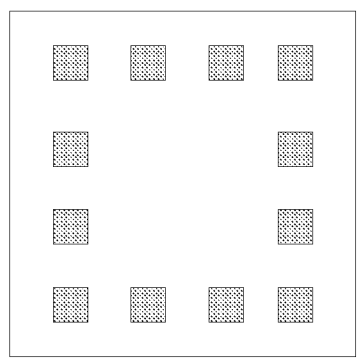
FIG. 17(b) illustrates a plan view and cross section view of an integrated system according to an embodiment of the present invention.
Figure 17B:
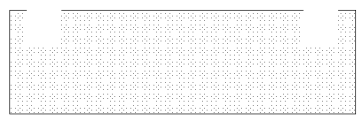

FIG. 17(b) shows an integrated system 1710 according to an embodiment of the present invention. Integrated system 1710 may include squares in the semiconductor die perimeter. The top section of FIG. 17(b) shows a plan view of the die with the squares, and the bottom section shows a cross section view with the squares. The squares may be formed on the back side of the semiconductor die with laser cuts or by an etching or some other process capable of providing the required deformation. The squares form ridges for an encapsulant to be embedded within thus more securely attaching the multiple layers to each other.

Figure 17C:
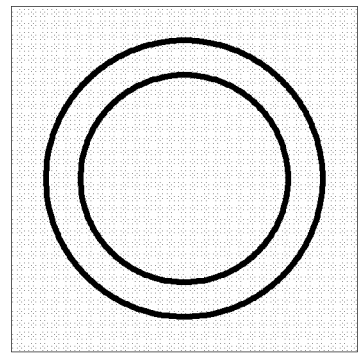
FIG. 17(c) illustrates a plan view and cross section view of an integrated system according to an embodiment of the present invention.
Figure 17C:
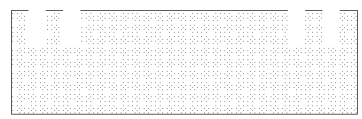

FIG. 17(c) shows an integrated system 1720 according to an embodiment of the present invention. Integrated system 1720 may include co-centric circles in the semiconductor die perimeter. The top section of FIG. 17(c) shows a plan view of the die with two co-centric circles, and the bottom section shows a cross section view with the two co-centric circles. The co-centric circles may be formed on the back side of the semiconductor die with laser cuts or by an etching or some other process capable of providing the required deformation. The co-centric circles form ridges for an encapsulant to embed within thus more securely attaching the multiple layers to each other.

Figure 17D:
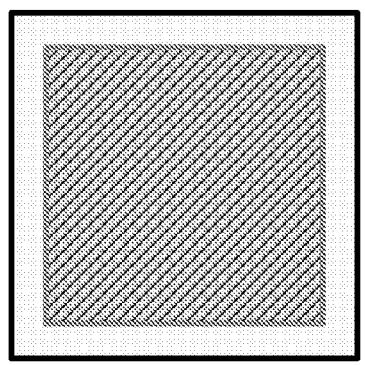
FIG. 17(d) illustrates a plan view and cross section view of an integrated system according to an embodiment of the present invention.
Figure 17D:
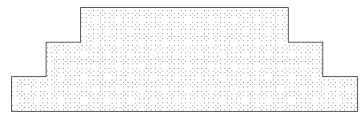

FIG. 17(d) shows an integrated system 1730 according to an embodiment of the present invention. Integrated system 1730 may include staggered steps in the semiconductor die perimeter. The top section of FIG. 17(d) shows a plan view of the die with the staggered steps, and the bottom section shows a cross section view with the staggered steps. The steps may be formed on the back side of the semiconductor die with laser cuts or by an etching or some other process capable of providing the required deformation. The steps form ridges for an encapsulant to embed within thus more securely attaching the multiple layers to each other.

The patterns and shapes employed may be optimized as necessary to improve adhesion and locking between layers. This may be achieved by increasing the surface area and also by providing a recess/trench/area (depending on pattern or shape used) into which a portion of the material to be joined fills/cures/hardens such that it is mechanically locked. The patterns and shapes used may be optimized to maximize the robustness of the complete vertically integrated structure (through the singulation process as well as through the operating life time of the system).

Figure 18:
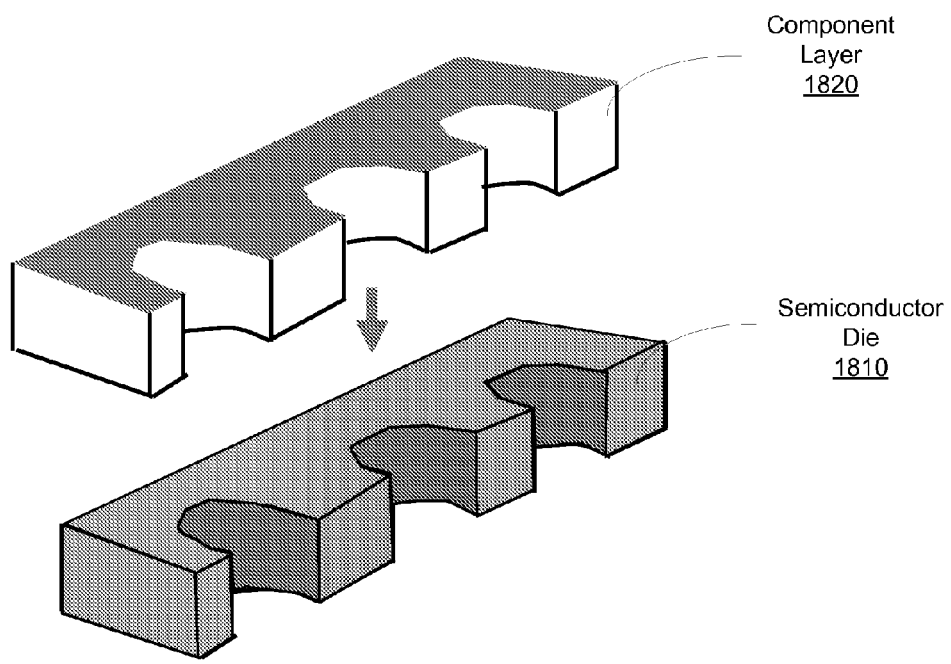
FIG. 18 illustrates a cross section view of an edge of an integrated system according to an embodiment of the present invention.

The integrated system according to the present invention may be embedded within a PCB type structure. Accordingly, the integrated system may incorporate further locking features to ensure that the integrated system may be securely embedded within a PCB type structure or other structures. FIG. 18 illustrates the edge of an integrated system according to an embodiment of the present invention. Both a semiconductor die 1810 and a component layer 1820 may have a serrated edge as shown or another shape profile to improve adhesion and thus allowing more securely embedding within a final substrate. The edge finish may be formed during the singulation process as described in further detail below.

Figure 19:
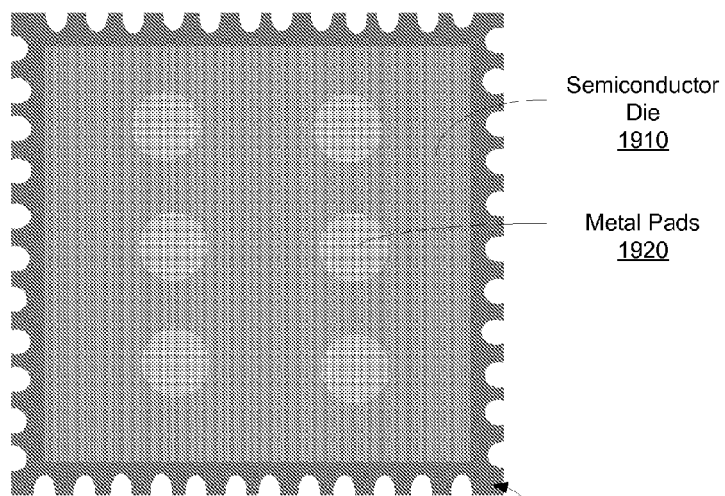
FIG. 19 illustrates a plan view and cross section view of an integrated system according to an embodiment of the present invention.
Figure 19:
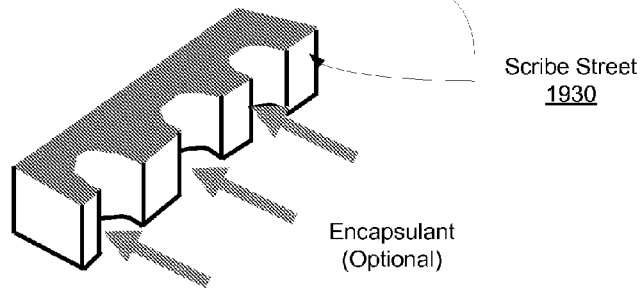

FIG. 19 further illustrates the edge finish in an integrated system 1900 in a plan view and cross-section view according to an embodiment of the present invention. Integrated system 1900 may include a semiconductor die 1910, metal pads 1920 in the active region, and scribe street 1930. The metal pads 1920 may be used for connection to another layer. The scribe street 1930 may include an edge finish such as a serrated edge producing gaps which may be subsequently filled by an encapsulant.

Figure 20:
FIG. 20 illustrates a scribe street of an integrated system according to an embodiment of the present invention.

FIG. 20 illustrates how the edge finish may be formed. A scribe street 2010 may be fabricated with openings 2020. The openings 2020 may be formed by laser cutting or other known techniques, and the openings 2020 may be circular as shown or another shape. A final cut 2030 for singulation of integrated systems may be made in the openings 2020 to produce the serrated edge finish shown in FIG. 19. The final cut 2030 may be made by a laser, dicing saw, or other known device.

Figure 21:
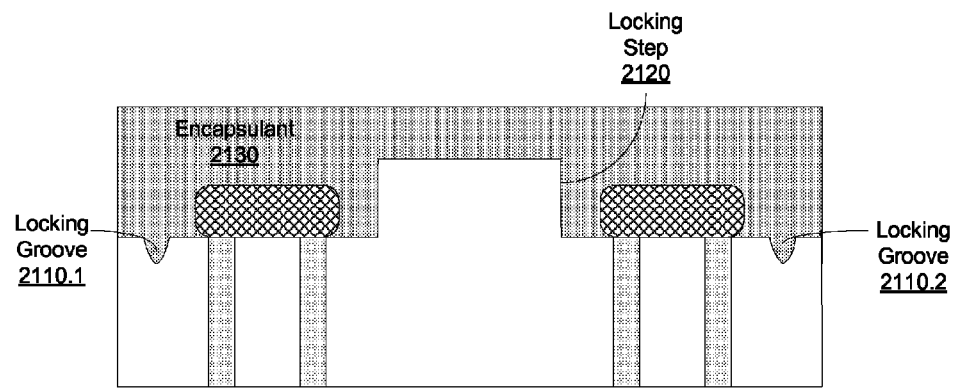
FIG. 21 is a block diagram of an integrated system according to an embodiment of the present invention.

FIG. 21 is a simplified block diagram of an integrated system 2100 according to another embodiment of the present invention. Integrated system 2100 shows the inter-connection of the two layers using locking features that improve adhesion between the two layers according to the present invention. Integrated system 2100 may include locking grooves 2110.1, 2110.2, a locking step 2120, and an encapsulant 2130.

The locking grooves 2110.1, 2110.2 may be located on the edges of the die similar to the embodiments shown in FIG. 17. The locking step 2120 may be a raised step from the surface where the passive components are mounted. The locking grooves 2110.1, 2110.2 may improve the robustness of the integrated system's construction because they secure the protected back side coating more firmly. As a result, the possibility of delamination or separation of the edge layers is greatly reduced. Since the back side layer is more securely adhered to die this also translates into the passive devices incorporated on the back side to be more securely adhered.

The locking grooves 2110.1, 2110.2 may formed by etching on the back side of the die. Moreover, encapsulant may be filled into the groove and the encapsulant may fill the opening and then harden to mechanically lock within the die. The locking groove 2110 adds more surface area of contact as compared to a flat surface thus improving adhesion. The same concept is true for the locking step 2120.

Figure 22:
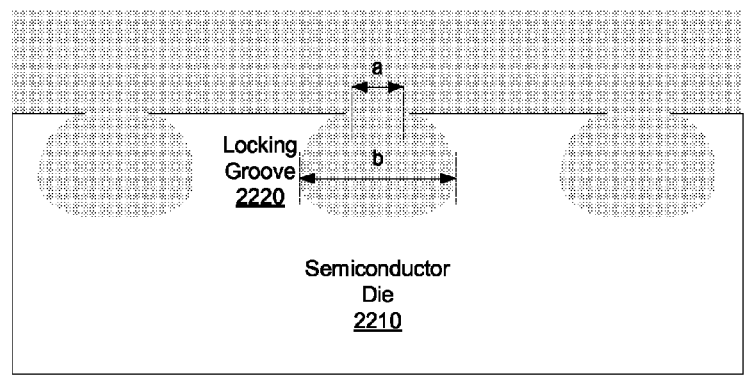
FIG. 22 illustrates a locking mechanism according to an embodiment of the present invention.

FIG. 22 shows a magnified view of a locking groove 2220 in order to illustrate how locking grooves improve adhesion. According to an embodiment of the present invention, adhesion may be further improved by etching a recess as shown in FIG. 22 where the widest portion of the groove, "b" is larger than the opening on the surface, "a". Since b>a, the surface area of contact is increased even further leading to improved adhesion.

Figure 23:
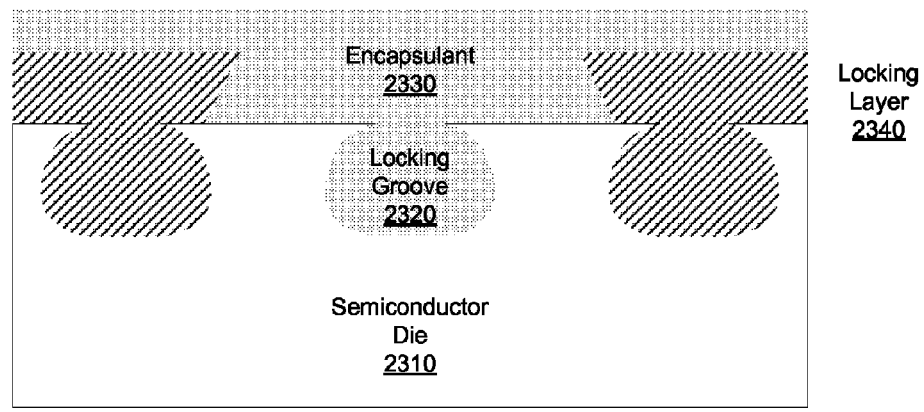
FIG. 23 illustrates a locking mechanism according to an embodiment of the present invention.

FIG. 23 is a simplified diagram of an integrated system 2300 according to another embodiment of the present invention that improves adhesion. Integrated system 2300 may include locking grooves 2320, an encapsulant 2330, and a locking layer 2340. In assembly, the locking layer 2340 may be added to a first set of grooves. Then the encapsulant 2330 may be added to a second set of grooves and also within the locking layer 2340. As the material at the interfaces between the layers deforms through heat, pressure, etc., and fills the grooves, the material will harden, which may mechanically lock and secure the entire integrated system as well as increasing the surface area which will also maximize adhesion. Opening features and surface patterns may be modified such as altering the shapes of the recesses/openings and staggering the locations within different layers for optimization to make the entire integrated system more robust.

Figure 24:
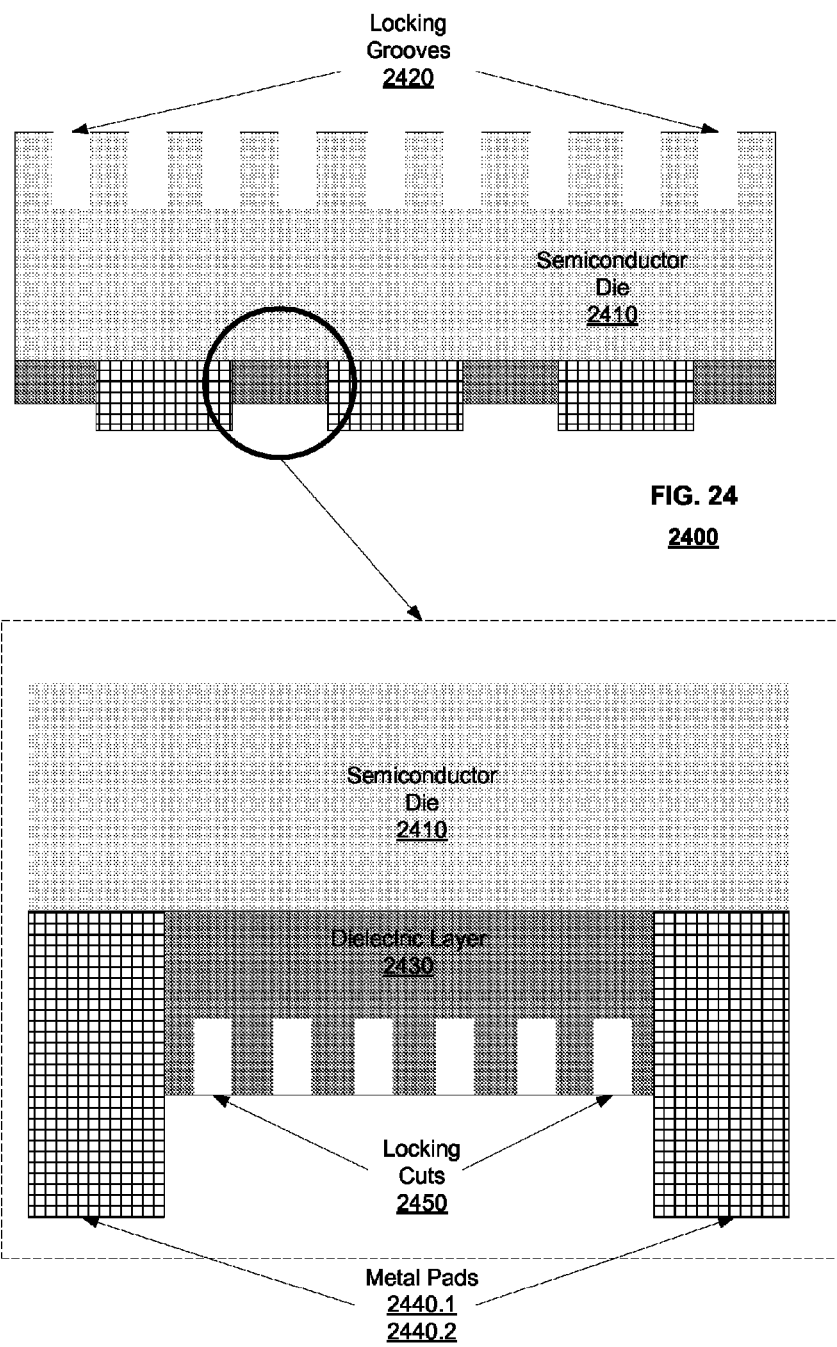
FIG. 24 is a block diagram of an integrated system according to an embodiment of the present invention.

According to an embodiment of the present invention, modifications may also be made on the active side the semiconductor die to improve adhesion. Integrated system 2400 of FIG. 24 illustrates such modifications. Integrated system 2400 may include a semiconductor die 2410, a dielectric layer 2430, metal pads 2440.1, 2440.2, and locking cuts 2450. The metal pads 2440.1, 2440.2 may be exposed metal contacts that are used to connect to the next packaging level such as a PCB. In between the metal pads 2440.1, 2440.2, the dielectric layer 2430 may include locking cuts 2450 that increase the surface area of contact thus improving adhesion. The locking cuts 2450 may be made as part of the bumping/wafer processing.

FIG. 25 shows a plan view of an active side that includes locking cuts or grooves that are capable of trapping or locking an encapsulant according to an embodiment of the present invention. Integrated system 2500 may include locking cuts 2550.1, 2550.2 and metal pad 2540. As shown, locking cuts 2550.1, 2550.2 may be co-centric circles etched in a top layer dielectric. The metal pad 2540 may be an exposed metal contact that is used to connect to the next packaging level such as a PCB.

Figure 26C:
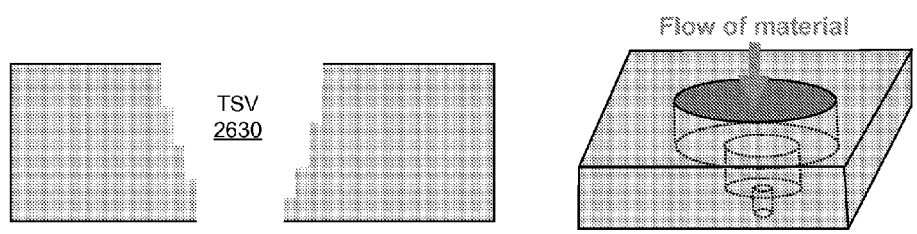
Figure 26D:
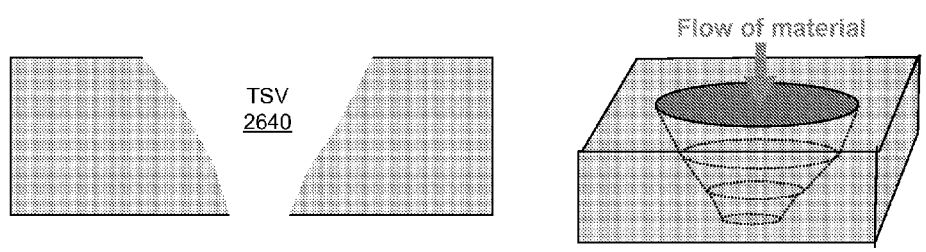

In another embodiment of the present invention, the shapes of the TSVs may be modified in order to improve adhesion of the conductive material contained within. For example, TSV opening on the back side of the semiconductor die may be modified so that the terminations of the passive components may be more securely embedded in the die making the entire integrated system more robust. FIG. 26(*a*) shows plan view of a TSV 2610 with a circular opening, and FIG. 26(*b*) shows a plan view of a TSV 2620 with an irregularly shaped opening. Both TSV 2610 and TSV 2620 may have the same radius r. In a plating process step, the TSV 2620 with the irregularly shaped opening has less volume within the via to be filled with conductive material as compared to the TSV 2610 with the circular opening. The TSV 2620 opening has a surface area less than the surface area of TSV 2610, which is $\pi *r^2$ for a circular opening. Therefore, TSV opening shapes may be modified to produce optimized adhesion effects for the conductive material within the via, making the integrated system more robust.

Moreover, separation and delamination of conductive layers within a via can cause serious issues for an integrated system. However, via construction according to embodiments of the present invention as described herein may hold conductive material more securely and, therefore, making the integrated system more robust.

As discussed below in more detail, an integrated system according to embodiments of the present invention may also be used in the analysis of fluids, gases, etc., and the vias may be used as conduit for movement between layers. Depending on the specific application, the vias may be constructed to optimize the flow of material through an opening to an optimal rate. FIG. 26(*c*) shows a cross section view of a TSV 2630 according to an embodiment of the present invention. TSV 2630 may include different stepped concentric openings such that the physical flow through the layer may be controlled to a specific rate. For example, the flow of material from the top of the layer to the bottom of the layer may be reduced because of TSV 2630's narrowing profile. FIG. 26(*d*) shows a cross section view of a TSV 2640 according to an embodiment of the present invention. TSV 2640 may include different sloped concentric openings such that the physical flow through the layer may be controlled to a specific desired rate. Alternatively, vias may be modified to produce a spiral of other optimized shapes in order to facilitate a desired rate of movement of fluid between levels. For example, the vias may be modified to act as part of a filtering or reduction of flow rate process so that pH levels may be monitored such as where the fluid passing through a specific layer or area within the vertically integrated system shows a discernible measured electrical value, and the layers are physically constructed to deliver a desired flow rate such that a fluid's pH may be continuously monitored.

Figure 27:
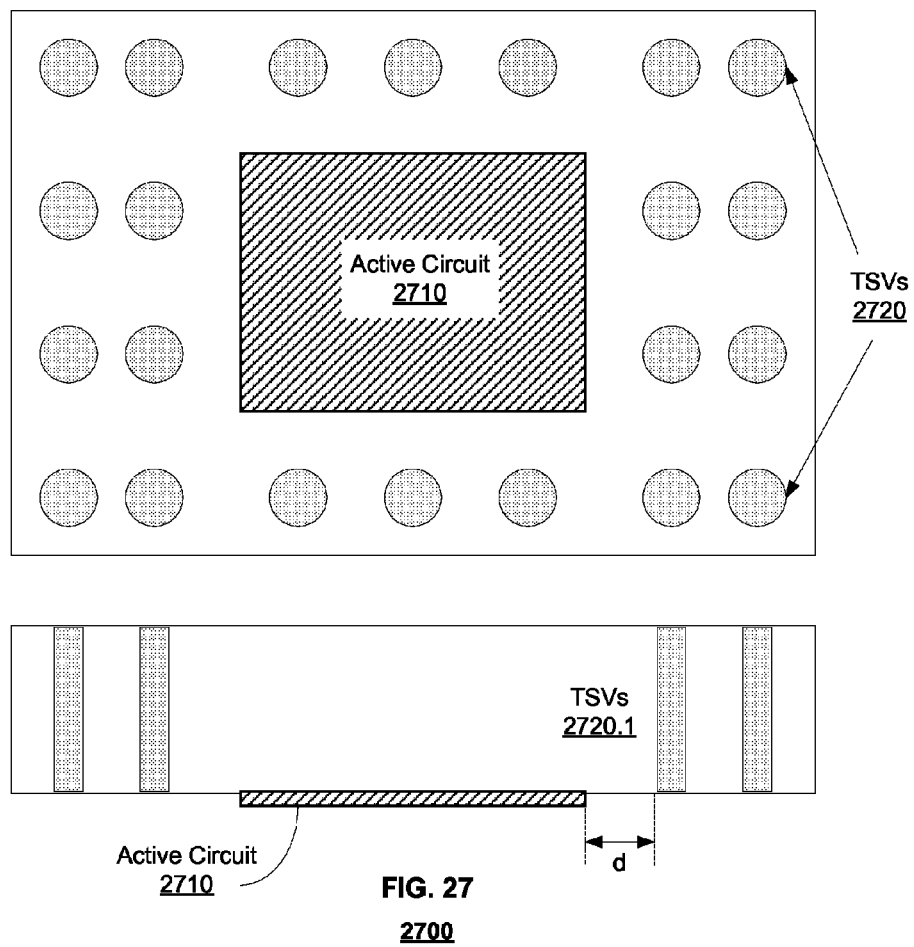
FIG. 27 illustrates a plan view and cross section view of an integrated system according to an embodiment of the present invention.

According to an embodiment of the present invention, TSVs may be placed in non-active areas of the semiconductor die because certain circuitry may have issues with TSVs directly above the active circuit. For example, the incorporation of vias above certain types of circuitry may cause mechanical stresses that could affect the performance of the system and cause parametric shift issues. FIG. 27 shows a plan view of the active side and a cross section view of an integrated system 2700 with an active circuit 2710 and a TSV array 2720. The TSV array 2720 may be located on the perimeter of the active circuit 2710 thus on the non-active area of the semiconductor die. Area "d" is the minimum distance between the active circuit 2710 and the closest TSV 2720.1 in order to minimize interference between the two parts.

Moreover, in another embodiment, TSVs may not be filled with conductive material depending on their application. For example, optical systems or cooling systems may employ TSVs that do not require conductive material to be filled therein. Therefore, non-conductive TSVs may still connect different layers of a vertically integrated system.

Figure 28:
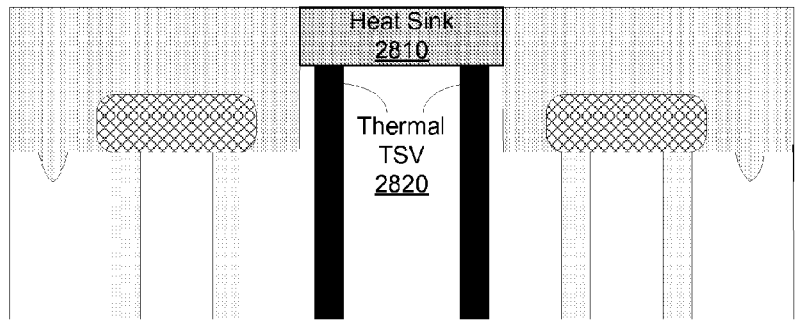
FIG. 28 is a block diagram of an integrated system according to an embodiment of the present invention.

Heating issues may arise with vertically integrated systems. The active circuit, as well as the passive components, may produce thermal heat when operating. Excessive heat can damage electrical parts and deteriorate overall performance of the integrated system. FIG. 28 is a simplified diagram of an integrated system 2800 according to another embodiment of the present invention. Integrated system 2800 may include a heat sink 2810 and thermal TSVs 2820. The heat sink 2810 may be a heat slug or a block of highly thermally conductive material. The heat sink 2810 in FIG. 28 is shown to be attached to a locking step; however, the heat sink 2810 may be attached to a cooling plate or other interfaces. The thermal TSVs 2820 may conduct heat from the active side to the back side of the die. Consequently, the heat sink 2810 and the thermal TSVs 2820 in conjunction dissipate heat produced from the active side preventing over-heating thus improving overall performance of the integrated system. Alternatively, the heat created by the system may be used to improve the overall efficiency of the integrated system (i.e., through using a thermoelectric generating layer) as described below. Moreover, the thermal TSVs 2820 used to transfer heat may be modified (e.g., enlarged) to optimize the thermal efficiency.

Figure 29:
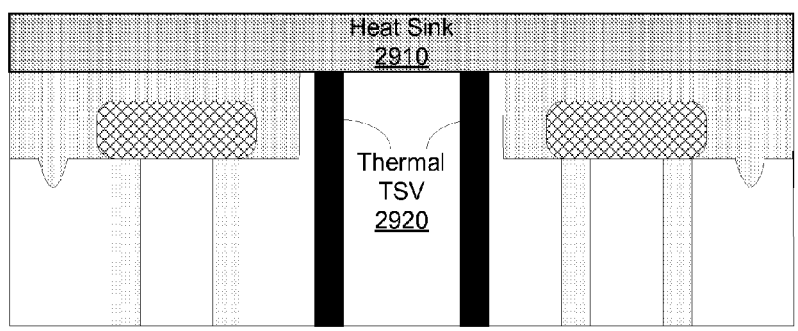
FIG. 29 is a block diagram of an integrated system according to an embodiment of the present invention.

FIG. 29 is a simplified diagram of an integrated system 2900 according to another embodiment of the present invention. Integrated system 2900 may include a heat sink 2910 and thermal TSVs 2920. The heat sink 2910 may be a heat slug or a block of highly thermally conductive material. The heat sink 2910 in FIG. 29 is shown to be attached to a locking step; however, the heat sink 2910 may be attached to a cooling plate or other interfaces. The thermal TSVs 2920 may conduct heat from the active side to the back side of the die. The heat sink 2910 may cover the active circuit on the active side entirely and may be more thermally efficient in dissipated heat than a heat sink that partially covers the active circuit. As the size of the heat sink increases, so does the heat sink's thermal efficiency because thermal efficiency is directly proportional to the heat sink's size.

Figure 30A:
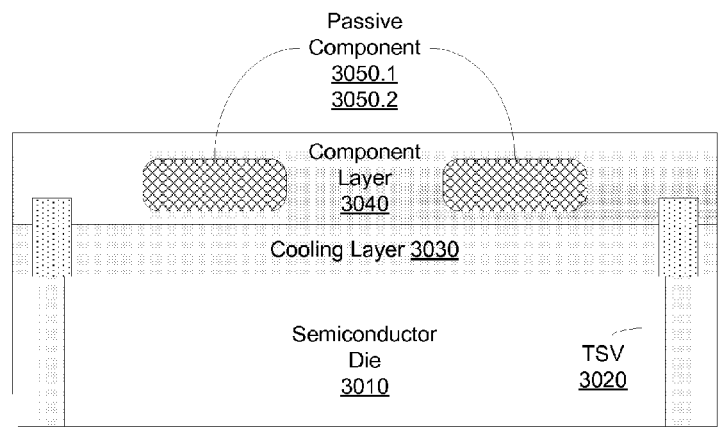
FIG. 30(a) is a block diagram of an integrated system according to an embodiment of the present invention.

According to another embodiment of the present invention, cooling layers may also be employed in dissipating heat generated in a vertically integrated system. FIG. 30(a) is a simplified diagram of an integrated system 3000 according to another embodiment of the present invention. Integrated system 3000 may include a semiconductor die 3010, TSVs 3020, a cooling layer 3030, and a component layer 3040 with passive components 3050.1, 3050.2. The component layer 3040 may be electrically coupled to an active circuit on the active side of the semiconductor die 3010 by TSVs 3020. The cooling layer 3030 may also include a via to support the electrical connection between component layer 3040 and the active circuit. The via in the cooling layer 3030 may or may not be thru silicon depending on the cooling layer material. The cooling layer 3030 may be a cooling plate or a micro fluidic system to optimize heat dissipation.

Figure 30B:
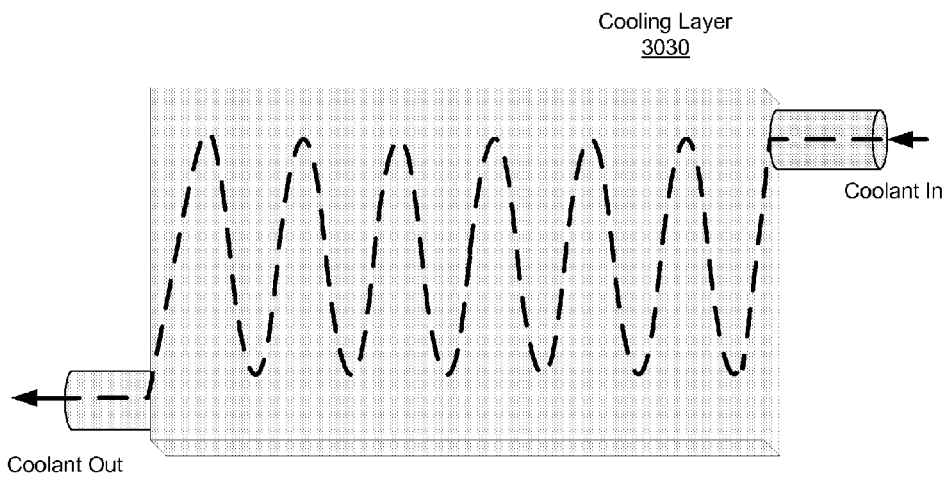
FIG. 30(b) illustrates a cooling layer according to an embodiment of the present invention.

FIG. 30(b) is a simplified diagram of one embodiment of cooling layer 3030. The cooling layer 3030 may include micro channels through which coolant material may be passed. The cooling layer 3030 may also accommodate a micro fluidic pump system to circulate coolant thus removing heat. The coolant may be inserted in one end and pumped through to the other end. As a result, the coolant circulation may lower the temperature in the integrated system.

Figure 31A:
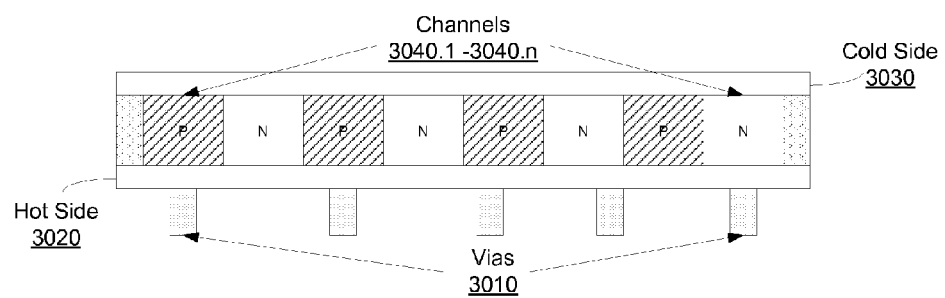
FIG. 31(a) illustrates a cooling layer according to an embodiment of the present invention.

FIG. 31(a) is a simplified diagram of another embodiment of a cooling layer 3100. The cooling layer 3100 may include peltier or thermoelectric type cooling system. The cooling layer 3100 may include a hot side 3020, a cold side 3030, and channels 3040.1-3040.n. The cooling layer 3100 may also be coupled to underneath layers by vias 3010. The vias 3010 may be thermal vias, and the vias 3010 may couple the cooling layer 3010, for example, to a heat sink or a PCB. The channels 3040.1-3040.n may be selectively used to dissipate heat to specific areas in the hot side 3020 and the vias 3010 coupled to the hot side in the specific area. The heat may then be dissipated through the vias 3020 preventing over-heating. In this embodiment, target heat dissipation into specific areas may be optimized. The system may be further optimized by directing the heat through these vias towards a thermoelectric layer. This layer may also be configured to apply cooling to specific areas within the vertically integrated system.

Figure 31B:
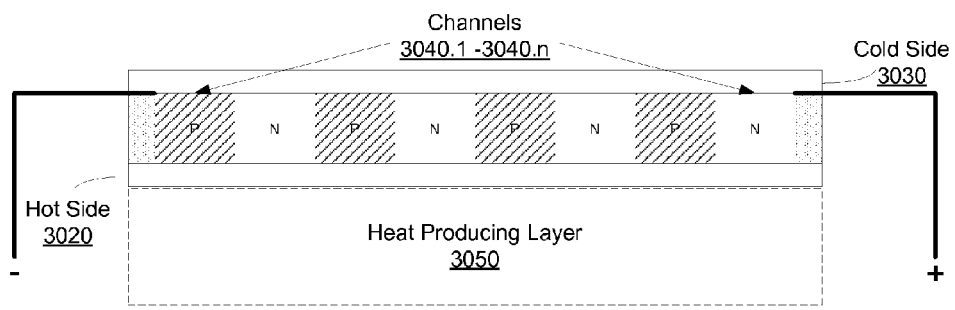
FIG. 31(b) illustrates a thermoelectric generating layer according to an embodiment of the present invention.

In addition to dissipating heat, the cooling layer may be used as a thermoelectric generating layer, where heat (for example generated from other components or layers within the vertically integrated system) is converted into electrical charge. FIG. 31(b) is a simplified diagram of an embodiment of a thermoelectric generating layer 3100.1. The thermoelectric generating layer 3100.1 may include a hot side 3020, a cold side 3030, and channels 3040.1-3040.n. The thermoelectric generating layer 3100.1 may also be coupled to underneath heat producing layers 3050, which may contain passive components or other high power components. The thermoelectric generating layer 3100.1 may use heat generated from within the system to generate electrical current, which can then be stored or redistributed within the system. The thermoelectric layer may be incorporated to maximize the amount of charge generated. For example, the hot side 3020 may be thermally connected to hot spots from within the system, and the cold side 3030 may also be connected to a cooling layer or to other structures such that the temperature differential between the hot and cold side 3020, 3030 respectively may be maximized and, thus, the maximum current may be generated). Therefore, the integrated system may harvest energy dissipated as heat and recycle it to power the integrated system and thus conserve power.

Figure 32:
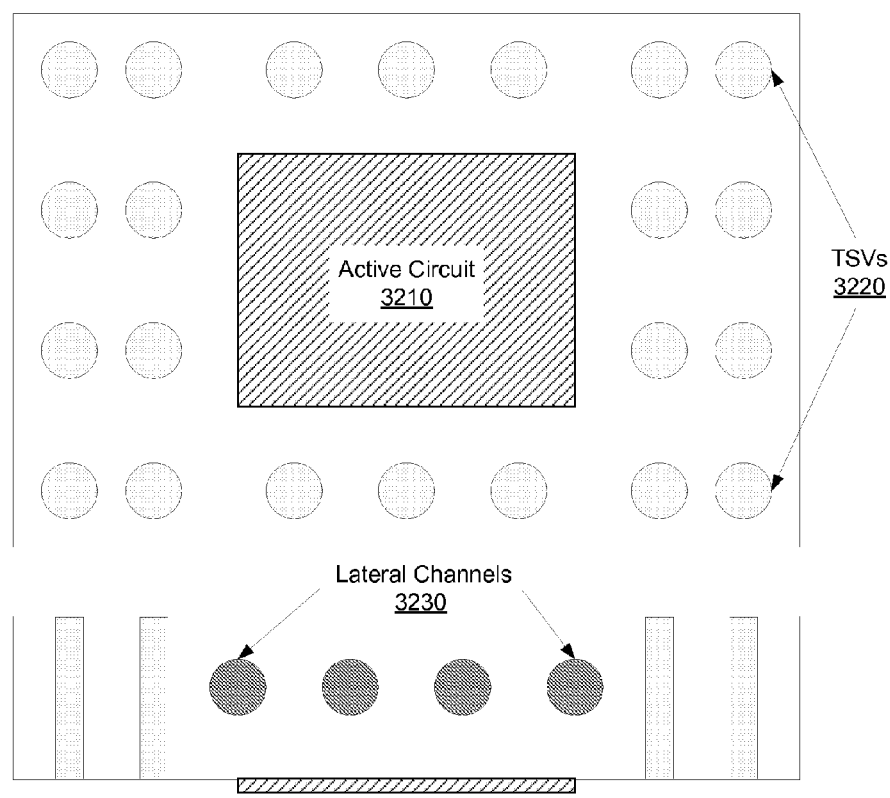
FIG. 32 illustrates a plan view and cross section view of an integrated system according to an embodiment of the present invention.

Moreover, lateral channels may be employed for heat dissipation needs. The lateral channels may also maximize the temperature differential between the hot and cold faces of the thermoelectric layers and, hence, maximize the generated charge. FIG. 32 is a simplified diagram of an integrated system 3200 according to another embodiment of the present invention. FIG. 32 shows a plan view of the active side and a cross section view of the integrated system 3200. The integrated system 3200 may include an active circuit 2710, a TSV array 3220, and lateral channels 3230. The lateral channels 3230 may be disposed in the semiconductor die above the active circuit 3210 and run parallel with front and back sides. The lateral channels 3230 may also be used to incorporate micro fluidic cooling, optical transmission systems, etc. Heat generated by the active circuit underneath the lateral channels may be dissipated by the lateral channels.

Figure 33A:
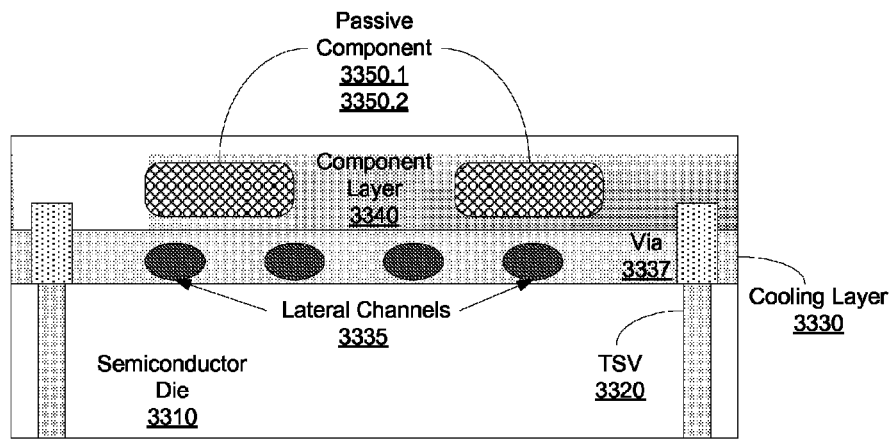
FIG. 33(a) is a block diagram of an integrated system according to an embodiment of the present invention.

Lateral channels may also be located in different layers of a vertically integrated system such as a cooling layer. FIG. 33(a) is a simplified diagram of an integrated system 3300 according to another embodiment of the present invention. Integrated system 3300 may include a semiconductor die 3310, TSVs 3320, a cooling layer 3330 with lateral channels 3335, and a component layer 3340 with passive components 3350.1, 3350.2. The component layer 3040 may be electrically coupled to an active circuit on the active side of the semiconductor die 3010 by TSVs 3320. The cooling layer 3330 may also include a via 3337 filled with conductive material to support the electrical connection between component layer 3340 and the active circuit. The via 3337 may or may not be thru silicon depending on the cooling layer material.

Figure 33B:
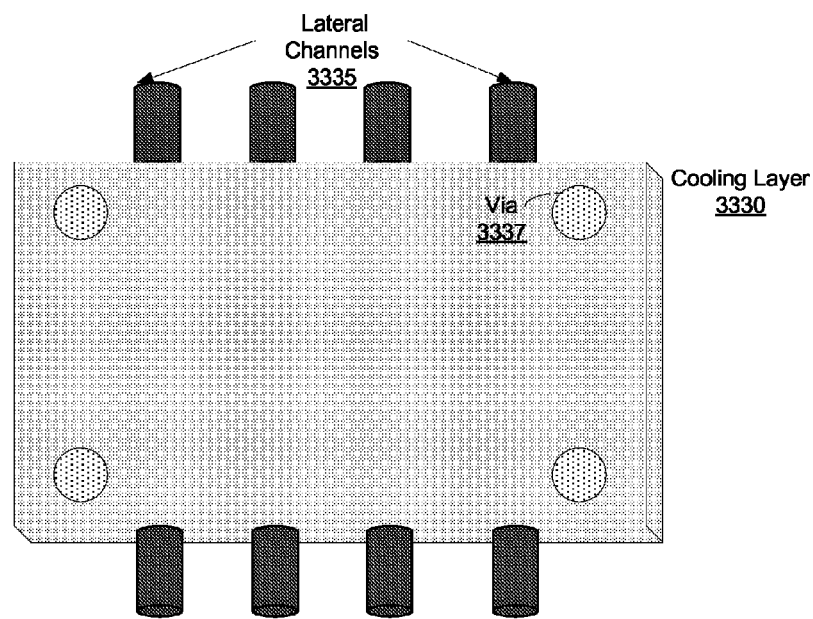
FIG. 33(b) illustrates a cooling layer according to an embodiment of the present invention.

FIG. 33(b) is a simplified diagram of one embodiment of cooling layer 3330 that incorporates a micro fluidic cooling system. The cooling layer 3330 may include lateral channels 3335 through which coolant material may be passed. The cooling layer 3330 may also accommodate a micro fluidic pump system to circulate coolant thus removing heat.

Figure 34A:
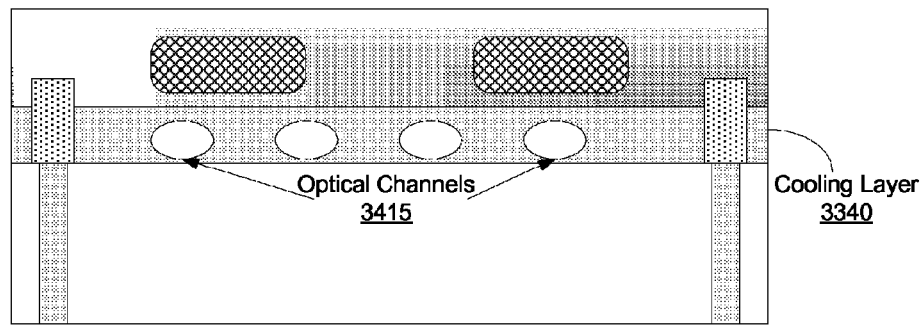
FIG. 34(a) is a block diagram of an integrated system according to an embodiment of the present invention.
Figure 34B:
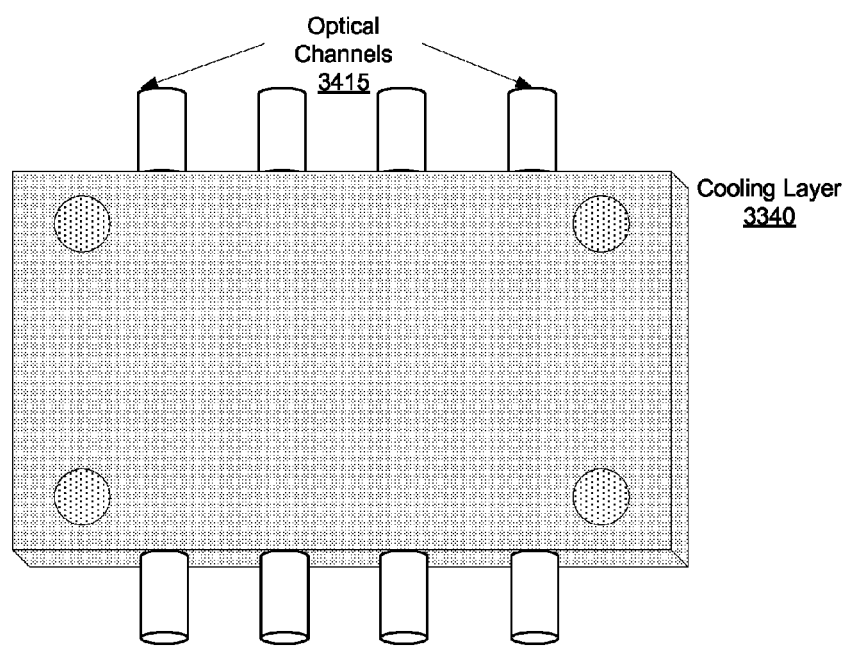
FIG. 34(b) illustrates a cooling layer according to an embodiment of the present invention.

Moreover, lateral channels may be used for other purposes than cooling systems. For example, optical transmission lines may be located in the lateral channels in order to provide communication links. FIG. 34(a) is a simplified diagram of an integrated system 3400 according to another embodiment of the present invention that is similar to integrated system 3300 of FIG. 33(a). Integrated system 3400 may include a cooling layer 3340 with lateral channels that operate as optical channels 3415 as shown in FIG. 34(b). The optical channels 3415 may include light pipes, fiber optics, etc. The optical isolation may also be utilized in energy harvesting applications. For example, when energy may be recycled back to a battery supply, boosted voltage levels (in excess of the applied supply voltage on the device) may be shuffled to the supply via an optically isolated link to avoid any potential negative effects of overloading the battery with any current or voltage surges. The optical channels may also be employed to actually boost voltages and create a secondary supply using a light source and a photodiode array to boost to desired voltage levels.

For some applications (e.g., haptics or touch screen technologies) a large voltage may be generated by the touching of a screen to access a function on the screen. As the different options are chosen, a charge is generated and has to be "dumped". An integrated system according to an embodiment of the present invention may provide a layer that contains structures (e.g., capacitors) that can store this "dumped" charge and then re-circulate it through the system. Therefore, the integrated system according to the present invention may harvest energy generated by different facets of the system to improve overall power efficiency.

Some integrated circuit applications may require analysis of materials such as fluids, gases, etc. Conventionally, a separate part outside the integrated circuit is usually required for the holding and measuring of the material that needs to be analyzed. According to an embodiment of the present invention, a measuring layer may be incorporated on the back side of a semiconductor die thus reducing the number of separate parts needed for a given application.

Figure 35A:
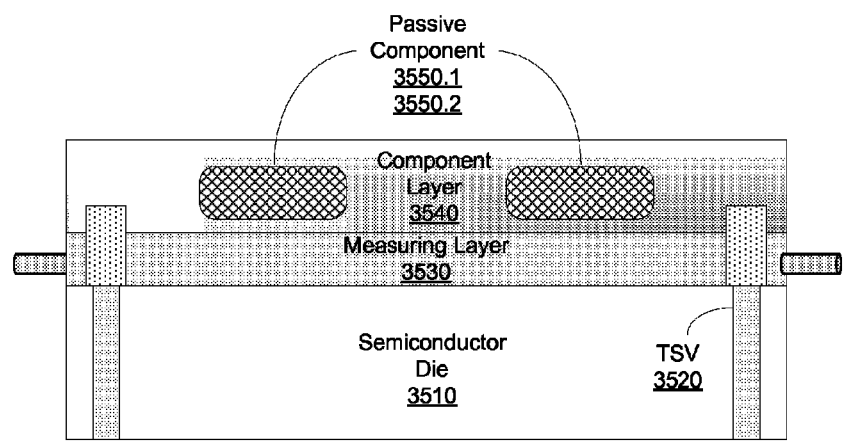
FIG. 35(a) is a block diagram of an integrated system according to an embodiment of the present invention.
Figure 35B:
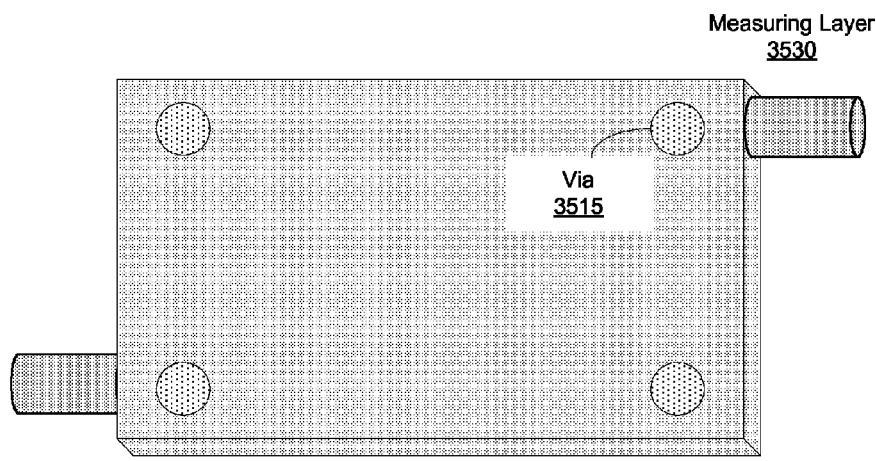
FIG. 35(b) illustrates a measuring layer according to an embodiment of the present invention.

FIG. 35(a) is a simplified diagram of an integrated system 3500 according to an embodiment of the present invention. Integrated system 3500 may include a semiconductor die 3510, TSVs 3520, a measuring layer 3530, and a component layer 3540 with passive components 3550.1, 3550.2. The measuring layer 3530 may include channels that can manipulate or analyze fluids or other materials being passed through it as shown in FIG. 34(b). For example, the measuring layer may monitor pH levels of a fluid, monitor the rate of flow for a liquid, monitor gas concentrations, etc.

The measuring layer 3530 may include electrical connections for coupling to above and underneath layers. The electrical connections may be vias filled with conducting material. The measuring layer 3530 may also include other electronic circuitry to provide an electrical signal representing the monitoring quantity and providing the signal to the other layers in the integrated system 3500. For example, the measuring layer 3530 may include electronic circuitry to produce an analog signal representing the pH level of a liquid being analyzed. Moreover, the measuring layer may further include electronic circuitry to provide filtration, separation, and analysis capability. For example, MEMS devices may be incorporated into the measuring layer. The measurement layer may also incorporate mechanical features and structures that optimize manipulation of a fluid, gas, etc.

Figure 36:
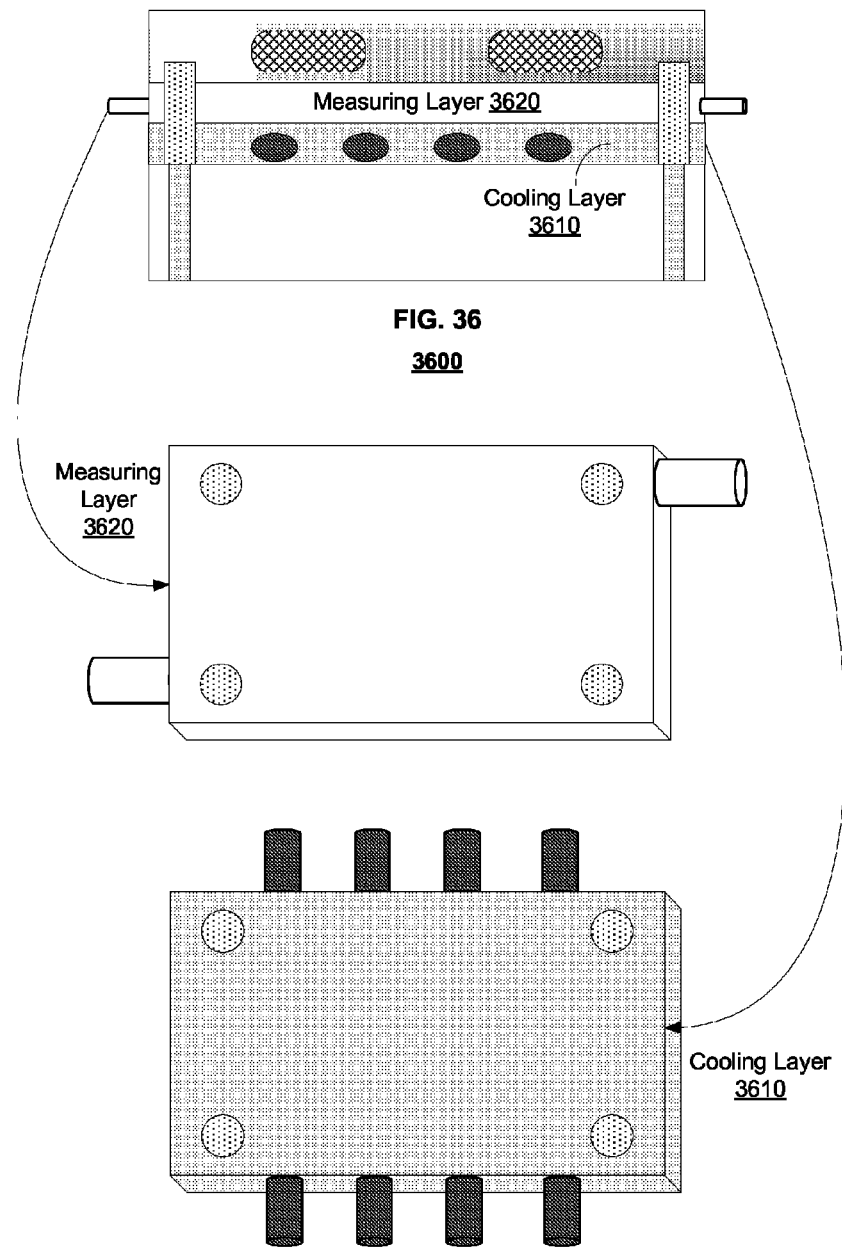
FIG. 36 is a block diagram of an integrated system, cooling layer, and a measuring layer according to an embodiment of the present invention.

FIG. 36 is a simplified diagram of an integrated system 3600 according to an embodiment of the present invention. Integrated system 3600 may include a cooling layer 3610 and a measuring layer 3620. The cooling layer 3610 may be similar to the cooling layers described above, and the measuring layer 3620 may be similar to the measuring layers described above. The cooling layer 3610 and measuring layer 3620 may work in conjunction to measure a material while cooling the integrated system 3600 because of the interaction between the layers. For example, the cooling layer 3610 may include heating elements that absorb heat from the active circuit.

The heating elements may also accelerate the processing of the material that is passing through the measuring layer 3620. Therefore, integrated system 3600 uses heat generated by one layer that is usually detrimental to the system to better operate another layer such as the measuring layer. For example, measuring layer 3620 may include channels for a liquid that is to be analyzed. Heat transported from the cooling layer 3620 may accelerate the movement of the liquid through the channels in the measuring layer leading to faster operations. Other analysis operations such as separation, filtration, etc., may also be accelerated by heat. Moreover, both the cooling layer 3610 and measuring layer 3620 may include other electronic circuitry that can communicate with the other layers in the integrated system 3600.

Figure 37:
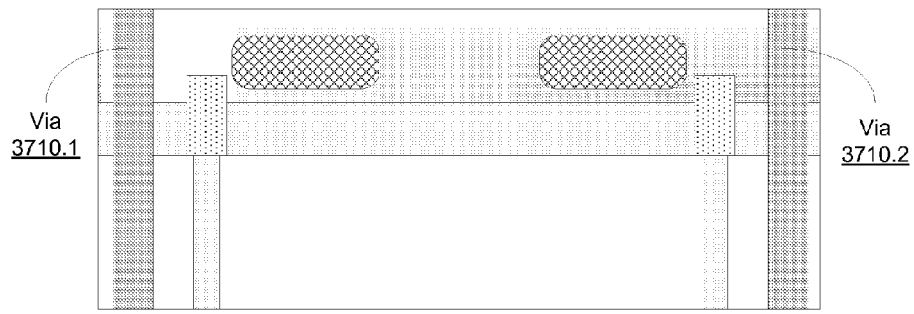
FIG. 37 is a block diagram of an integrated system according to an embodiment of the present invention.

According to another embodiment of the present invention, a via through different layers of a vertically integrated system may be used as a channel for analysis. FIG. 37 is a simplified diagram of an integrated system 3700 according to an embodiment of the present invention. Vias 3710.1, 3710.2 may pass thru some or all the layers of integrated system 3700. The vias 3710.1, 3710.2 may manipulate or analyze fluid or other materials such as gases that pass through the vias. One layer in integrated system 3700 may include electronic circuitry, for example MEMS, that provide analysis operations such as separation, filtration, etc.

Figure 38:
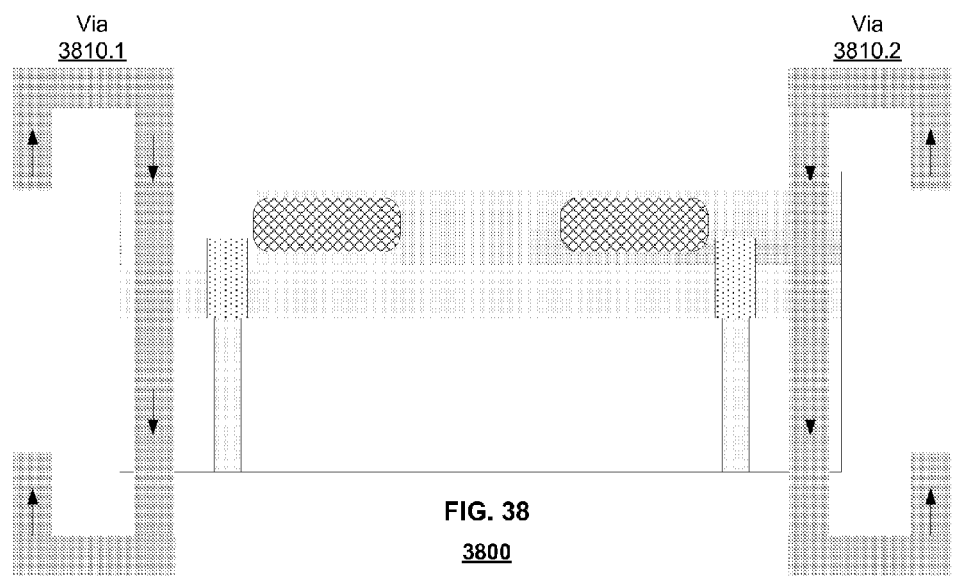
FIG. 38 is a block diagram of an integrated system according to an embodiment of the present invention.

One benefit of the via design is that it conserves power. Gravity may transport the material in the vias within the integrated system. Therefore, less power will be required by the integrated system. FIG. 38 illustrates how a material may pass through the vias 3810.1, 3810.2. The arrows show how gravity may move the material through the integrated system 3800 from the top layer to the bottom layer. The specific design of these vias may be modified as required to suit specific applications.

Figure 39:
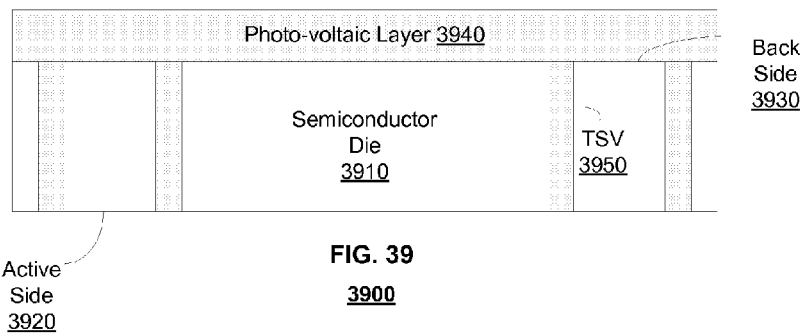
FIG. 39 is a block diagram of an integrated system according to an embodiment of the present invention.

Other power saving techniques may be employed in vertically integrated systems according to the present invention. FIG. 39 is a simplified diagram of an integrated system 3900 according to an embodiment of the present invention. Integrated system 3900 may include a semiconductor die 3910 with an active side 3920 and a back side 3930, a photo-voltaic layer 3940, and TSVs 3950. The photo-voltaic layer 3940 may be formed or mounted on the back side 3930 and may be modifiable with laser trimming. The photo-voltaic layer 3940 may include organic photo-voltaic cells that transform solar rays into electrical energy. The cells may include transparent conductive electrodes that allow light to couple to active materials thus creating electrical energy. The electrical energy may then power the integrated system 3900 thus providing a self-powered system.

Figure 40A:
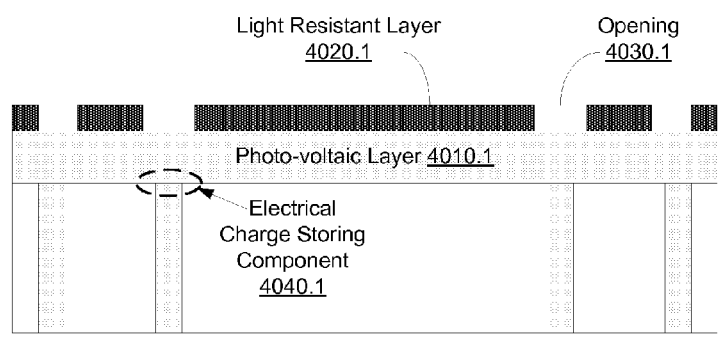
FIG. 40(a) is a block diagram of an integrated system according to an embodiment of the present invention.
Figure 40B:
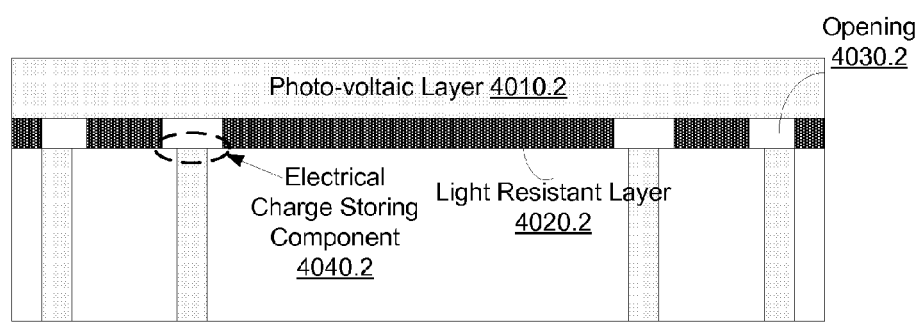
FIG. 40(b) is a block diagram of an integrated system according to an embodiment of the present invention.

FIG. 40(*a*) is a simplified diagram of an integrated system 4000 according to an embodiment of the present invention. Integrated system may include a photo-voltaic layer 4010.1, a light resistant layer 4020.1 with openings 4030.1, and electrical storage components 4040.1. The light resistant layer 4020.1 may be disposed on top of the photo-voltaic layer and may include strategically placed openings 4030.1. The light resistant layer 4020.1 may serve several purposes. The light resistant may protect other electrical parts in the integrated system 4000 that can be damaged by light exposure. The light resistant layer 4020.1 through the openings 4030.1 may also be patterned to control the flow of light and current. The openings 4030.1 may be optimized to maximize the current flow from the photo-voltaic layer 4010.1 to other layers underneath. Moreover, electrical storage components 4040.1 may be located in the regions underneath the openings 4030.1 in order to store and manipulate electrical charges produced by the photo-voltaic layer 4010.1. The active circuit may control the operation of the electrical storage components 4040.1. For example, the active circuit may access certain electrical storage components when the application requires the use of certain components. Therefore, power usage may be efficiently controlled by the active circuit. Alternatively, a light resistant layer may incorporate strategically placed photo-voltaic cells to generate charge in specific areas. Furthermore, light pipes and other light transmitting devices may be used to divert, channel and concentrate light from external sources to specific photo-voltaic cells within the integrated system and, thus, maximize the charge generated.

The photo-voltaic layer and light resistant layer may be transposed with the photo-voltaic layer being on top of the light resistant layer. FIG. 40(*b*) is a simplified diagram of an integrated system 4001 according to an embodiment of the present invention. Integrated system 4001 may include a photo-voltaic layer 4010.2, a light resistant layer 4020.2 with openings 4030.2, and electrical storage components 4040.2. In this embodiment, the photo-voltaic layer 4010.2 may be on top of the light resistant layer 4020.2 and may be the top-most layer. Charge produced by the photo-voltaic layer 4010.2 is proportional to the area exposed to light. Thus, positioning the photo-voltaic layer 4010.2 on top may maximize the amount of charge produced. Also, selective patterning of the light resistant layer 4020.2 may protect some areas of the integrated circuit from light exposure.

Figure 41:
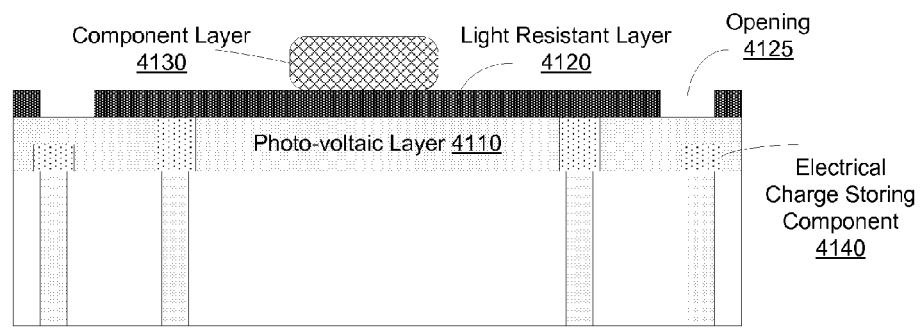
FIG. 41 is a block diagram of an integrated system according to an embodiment of the present invention.

Vertically integrated systems may be arranged in different manners depending on their applications. FIG. 41 is a simplified diagram of an integrated system 4100 according to an embodiment of the present invention. The integrated system 4100 may include a photo-voltaic layer 4110, a light resistant layer 4120 with openings 4125, a component layer 4130, and electrical storage components 4140. The component layer 4130 may include passive components. The light resistant layer 4120 may be underneath the component layer 4130, and the photo-voltaic layer 4110 may be underneath the light resistant layer 4120. Since the photo-voltaic layer 4110 is underneath a few layers, the openings 4125 may be strategically patterned to maximize the current flow from the photo-voltaic layer 4010 to other layers underneath. Also, the component layer 4130, in this embodiment, also may be strategically positioned so as to not cover the openings. Moreover, electrical storage components 4140 may be located in the regions underneath the openings 4125 in order to store and manipulate electrical charges produced by the photo-voltaic layer 4110. The active circuit may control the operation of the electrical storage components 4140.

Figure 42:
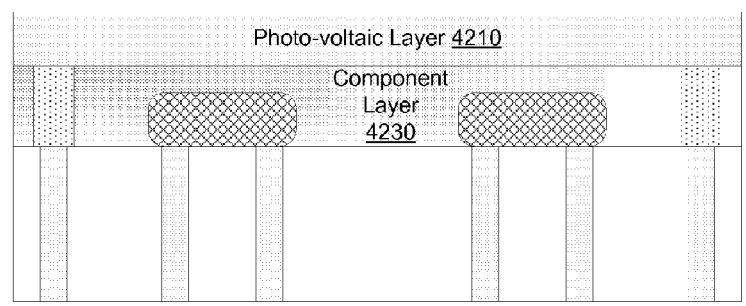
FIG. 42 is a block diagram of an integrated system according to an embodiment of the present invention.

In other embodiments, a photo-voltaic layer may be placed as top-most layer in a vertically integrated system. FIG. 42 is a simplified diagram of an integrated system 4200 according to an embodiment of the present invention. In integrated system 4200, a component layer 4230 with passive components, may be underneath a photo-voltaic layer 4210. Since the photo-voltaic 4230 layer is the top-most layer, it increases the surface area for light exposure. Thereby, increasing the amount of electrical energy produced.

Figure 43:
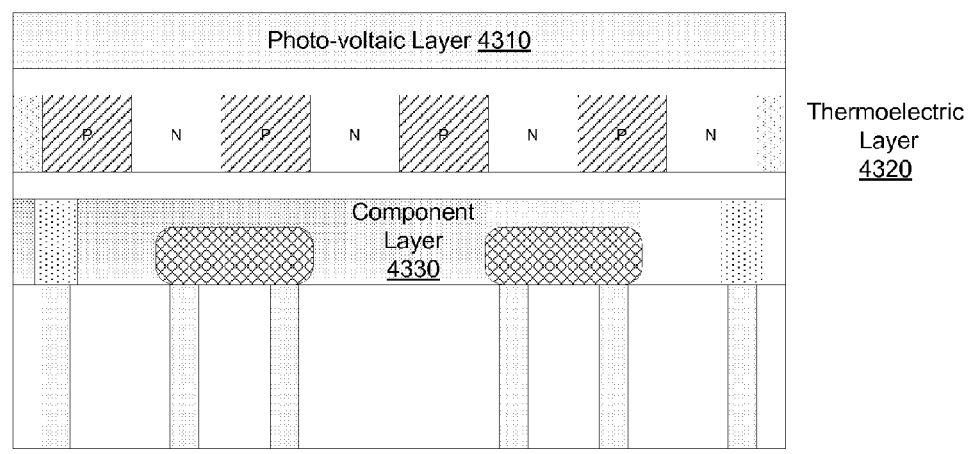
FIG. 43 is a block diagram of an integrated system according to an embodiment of the present invention.

In other embodiments, a photo-voltaic layer may work in conjunction with a thermoelectric layer. FIG. 43 is a simplified diagram of an integrated system 4300 according to an embodiment of the present invention. In integrated system 4300, a photo-voltaic layer 4310 may be provided on top of a thermoelectric layer 4320 and a component layer 4330 with passive components. The thermoelectric generating layer 4320 may include a hot side, a cold side, and channels. The thermoelectric generating layer 4320 may use heat generated from within the system to generate electrical current (harvest charge), which can then be stored or redistributed within the system. In addition, the thermoelectric generating layer 4320 may also harvest charge from the photo-voltaic layer 4310. The integrated system 4300 may include components such as capacitors to store the harvested charge. Furthermore, the links between the layers carrying the charge may be modified to improve rate of movement of current. The energy efficiency of the integrated system may be greatly improved through harvesting the heat produced within the system and also the charge produced form other sources such as a photo-voltaic layer. The harvested charge may be stored and redistributed throughout the system, for example, to charge a battery.

Figure 44:
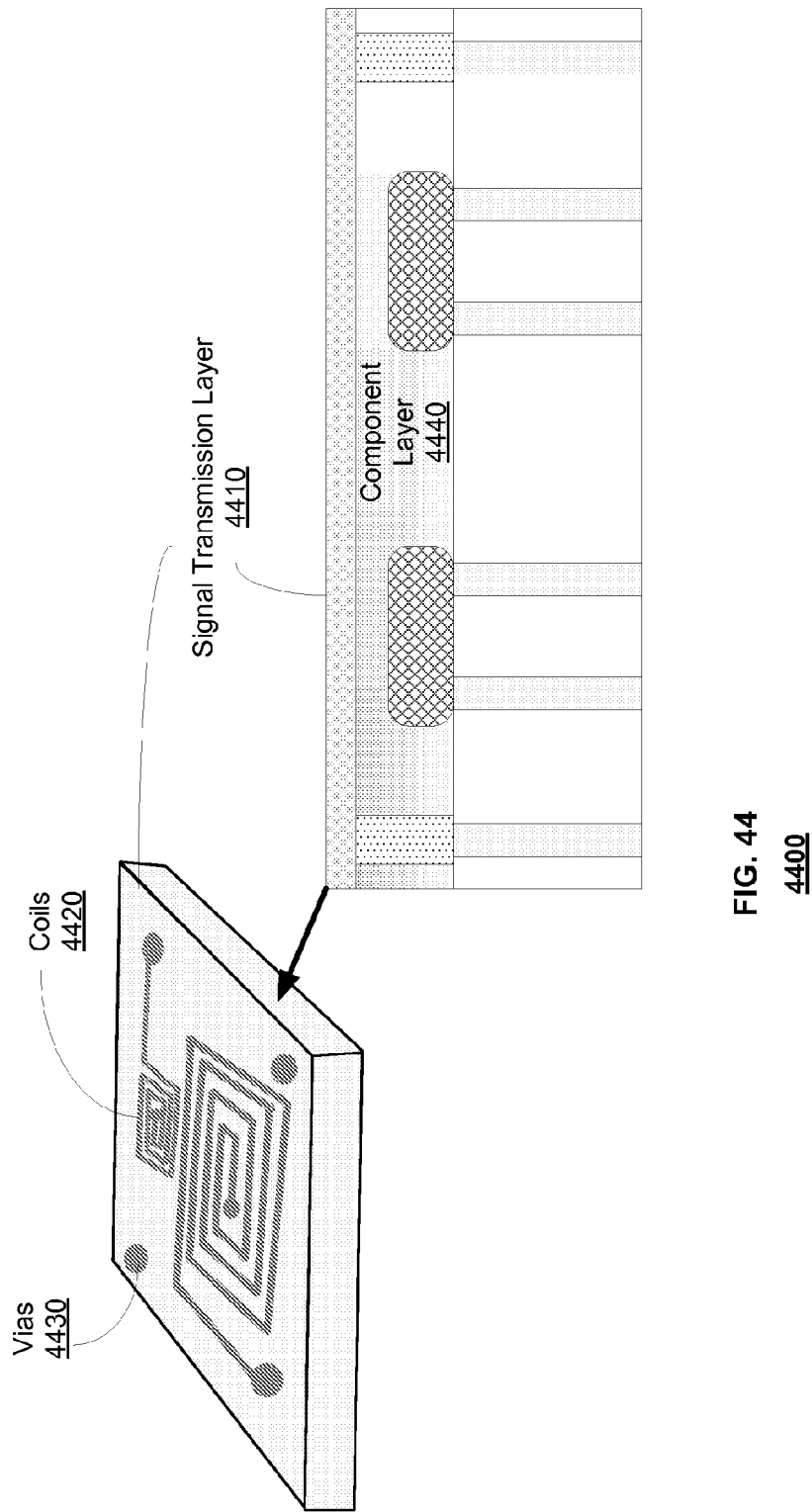
FIG. 44 is a block diagram of an integrated system according to an embodiment of the present invention.

In one application of an integrated system according to the present invention, the integrated system may be employed in a monitoring system such as an alarm system. FIG. 44 is a simplified diagram of an integrated system 4400 according to an embodiment of the present invention. The integrated system 4400 may include a signal transmission layer 4410 and a component layer 4440. The integrated system 4400 may also include other components described herein in other embodiments. The signal transmission layer 4410 may include coils 4420, such as inductor coils, and vias 4430 that may connect to other layers within the integrated system. Upon measuring a certain condition, coils 4420 may generate a resultant signal. The resultant signal may then be transmitted from the integrated system to another remote location, for example an alarm command center. For example, the integrated system may monitor the pH level of a fluid and if the monitored pH level exceeds a predetermined level, the integrated system may transmit the resultant signal.

In another embodiment, an integrated system according to the present invention may include an inductor in one layer that is capable of receiving a remote signal. The reception of the remote signal may activate the integrated system or a portion thereof. Inductive coils may be strategically positioned throughout the integrated system to activate/deactivate different portions and functionalities of the integrated system.

Additionally, an integrated system according to the present invention may incorporate remote sensing conduits such as thermocouples or fiber optic links. The remote sensing conduits may allow remote input feed to a layer within the integrated system. For example, a thermocouple with a sensing element may be placed in a harsh environment such as a high temperature environment. The thermocouple may then communicate with a layer within the integrated system and provide important information that would otherwise be unattainable.

Figure 45:
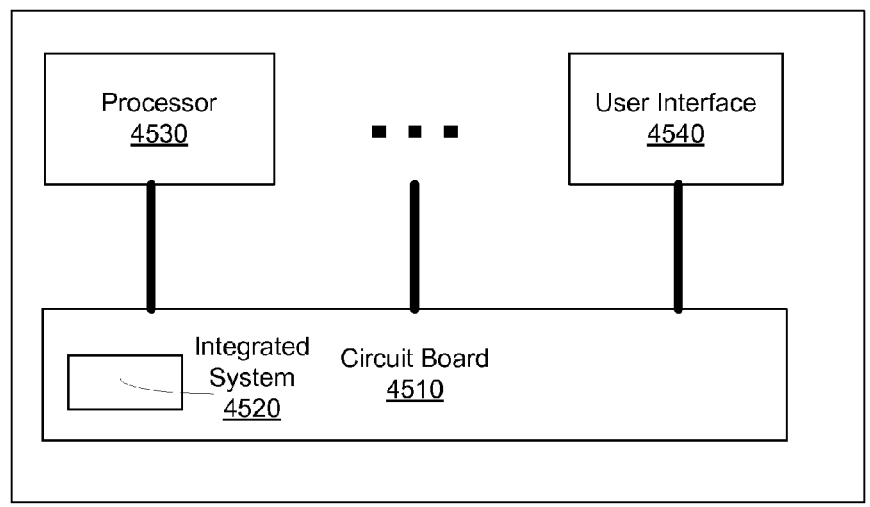
FIG. 45 is a block diagram of an electronic device according to an embodiment of the present invention.

The integrated system according to the present invention may be used in a variety of electronic devices and applications. FIG. 45 is a simplified block diagram of an electronic device 4500 according to an embodiment of the present invention. The electronic device 4500 may include a circuit board 4510 that may have an integrated system 4520 mounted on or within the circuit board 4510. The integrated system 4520 may include components described herein in other embodiments. The circuit board 4510 may be coupled to other components of the electronic device 4500 such as a processor 4530, a user interface 4540, and other suitable electrical components.

The processor 4530 may control the operations of the electronic device 4500 and its components. The processor 4500 may be any of a, or combination of, conventional processing systems, including microprocessors, digital signal processors, and field programmable logic arrays.

The user interface 4540 may include a display such as an LCD screen, a CRT, a plasma screen, an LED screen or the like. The user interface 4540 may be a keyboard, a mouse, touch screen sensors or any other user input device that would allow a user to interact with the electronic device 4500. The user interface 4540 may include hard keys and/or soft keys. The user interface 4540 may be integrated with a display in the form of a touch screen display, for example. The electronic device 4500 may include other components depending on the electronic device application. The electronic device 4500 may be a portable electronic device such as a digital camera, a cellular phone, an alarm system, a gaming device, or the like that may benefit from incorporation of an integrated system according to the present invention. The incorporation of an integrated system according to the present invention may reduce the size of the electronic device while maximizing performance.

Several embodiments of the present invention are specifically illustrated and described herein. However, it will be appreciated that modifications and variations of the present invention are covered by the above teachings and within the purview of the appended claims without departing from the spirit and intended scope of the invention. Furthermore, it will be appreciated that different components from different embodiments may be used in combination without departing from the spirit and intended scope of the invention. In other instances, well-known operations, components and circuits have not been described in detail so as not to obscure the embodiments. It can be appreciated that the specific structural and functional details disclosed herein may be representative and do not necessarily limit the scope of the embodiments.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

We claim:

1. An integrated circuit system, comprising:
an active layer fabricated on a front side of a semiconductor die;
an electrical component layer integrated with the semiconductor die;
a fluid holding layer disposed on a back side of the semiconductor die, the fluid holding layer including a channel for a fluid to flow;
at least one conductive path configured to electrically connect the active layer and the electrical component layer; and
at least one non-conductive path configured to connect pass the fluid between different layers in the integrated circuit system.

2. The integrated circuit system of claim 1, wherein the at least one non-conductive path has a narrowing profile from top to bottom of the integrated circuit system.

3. The integrated circuit system of claim 1, wherein the at least one non-conductive path has an inverted profile from top to bottom of the integrated circuit system.

4. The integrated circuit system of claim 1, wherein the at least one non-conductive path has profile that includes different concentric openings.

5. The integrated circuit system of claim 1, wherein the fluid holding layer includes a micro fluidic pump system.

6. The integrated circuit system of claim 1, wherein the at least one non-conductive path is above a non-active area of the active layer.

7. The integrated circuit system of claim 1, wherein the electrical component layer is disposed on the back side of the semiconductor die and comprises a discrete passive component electrically connected to the active layer by way of the at least one conductive path.

8. The integrated circuit system of claim 7, further comprising a measurement layer disposed on the back side of the semiconductor die, the measurement layer configured to measure a property of the fluid.

9. An integrated circuit system, comprising:
an active layer on a front side of a semiconductor die;
a fluid holding layer integrated with the semiconductor die, the fluid holding layer including a channel for a fluid to flow;
at least one conductive path configured to electrically connect different layers in the integrated circuit system;
at least one non-conductive path configured to pass the fluid between different layers in the integrated circuit system; and
a measurement layer integrated with the semiconductor die and configured to measure a property of the fluid in the fluid holding layer.

10. The integrated circuit system of claim 9, wherein the measurement layer includes circuitry configured to provide processing functions for the measurement.

11. The integrated circuit system of claim 10, wherein the circuitry includes a MEMS device.

12. The integrated circuit system of claim 9, wherein the property is a pH level of the fluid.

13. The integrated circuit system of claim 9, further comprising:
a signal transmission layer configured to transmit a measured result from the measurement layer external of the integrated circuit system.

14. The integrated circuit system of claim 13, wherein the signal transmission layer includes a coil.

15. The integrated circuit system of claim 9, wherein the measurement layer is configured to receive the fluid by way of the channel in the fluid holding layer.

16. The integrated circuit system of claim 9, wherein the fluid holding layer is disposed on a back side of the semiconductor die, and wherein the measurement layer is disposed on the back side of the semiconductor die.

17. The integrated circuit system of claim 16, wherein the measurement layer includes a MEMS device.

18. The integrated circuit system of claim 16, wherein the property is a pH level of the fluid.

19. The integrated circuit system of claim 16, further comprising a signal transmission layer configured to transmit a measured result from the measurement layer external to the integrated circuit system.

20. The integrated circuit system of claim 16, wherein the at least one conductive path is configured to electrically connect the measurement layer to another layer in the integrated circuit system.

21. A monitoring device, comprising:
a circuit board; and
a vertically integrated circuit on the circuit board, comprising:
an active layer fabricated on a front side of a semiconductor die;
a fluid holding layer integrated with the semiconductor die, the fluid holding layer including a channel for a fluid to flow;
a measurement layer integrated with the semiconductor die and configured to measure a property of the fluid; and
at least one conductive path configured to electrically connect different layers in the vertically integrated circuit.

22. The device of claim 21, further comprising a processor.

23. The device of claim 21, further comprising a signal transmission layer in the vertically integrated circuit configured to transmit an indication of the property.

24. The device of claim 21, further comprising a non-conductive path configured to pass the fluid to different layers in the vertically integrated circuit.

25. The device of claim 21, wherein the fluid holding layer is disposed on a back side of the semiconductor die, and wherein the measurement layer is disposed on the back side of the semiconductor die.

26. The device of claim 25, further comprising a non-conductive path configured to pass the fluid between different layers in the vertically integrated circuit, wherein the non-conductive path has a structure configured to manipulate the fluid such that the fluid flows at a desired rate.

27. The device of claim 25, further comprising a non-conductive path configured to receive the fluid from external to the vertically integrated circuit.

28. The device of claim 25, wherein the measurement layer comprises circuitry configured to provide processing functions to measure the property of the fluid.

29. An integrated circuit system, comprising:
a semiconductor die comprising an active layer;
an electrical component layer integrated with the semiconductor die, the electrical component layer comprising an electrical component;
at least one conductive path configured to electrically connect the active layer and the electrical component; and
a fluid holding layer integrated with the semiconductor die, the fluid holding layer including a channel for a fluid to flow.

30. The integrated circuit system of claim 29, wherein the semiconductor die is a silicon die and the at least one conductive path comprises a through silicon via filled with conducting material.

31. The integrated circuit system of claim 29, further comprising a measurement layer configured to measure a property of the fluid in the fluid holding layer.

32. The integrated circuit system of claim 29, further comprising a non-conductive path configured to pass the fluid between different layers in the integrated circuit system.

33. The integrated circuit system of claim 32, wherein the non-conductive path has a structure configured to manipulate the fluid such that the fluid flows at a desired rate.

34. The integrated circuit system of claim 32, wherein the non-conductive path is configured to receive the fluid from external to the integrated circuit system.

35. The integrated circuit system of claim 29, wherein the fluid holding layer is on a side of the semiconductor die opposite the active layer and wherein the electrical component layer is on the side of the semiconductor die opposite the active layer.

36. The integrated circuit system of claim 35, wherein the fluid holding layer is stacked vertically with the semiconductor die.

37. The integrated circuit system of claim 29, wherein the electrical component is a discrete passive component.

38. The integrated circuit system of claim 29, wherein the electrical component is a MEMS component configured to provide a processing function associated with analyzing the fluid.

* * * * *